United States Patent [19]
Cesarman et al.

[11] Patent Number: 6,093,806
[45] Date of Patent: *Jul. 25, 2000

[54] DNA ENCODING PROTEINS OF KAPOSI'S SARCOMA ASSOCIATED HERPESVIRUS

[75] Inventors: Ethel Cesarman, Hoboken, N.J.; Daniel M. Knowles, Forest Hills, N.Y.

[73] Assignee: Cornell Research Foundation, Inc., Ithaca, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/728,603

[22] Filed: Oct. 10, 1996

[51] Int. Cl.$^7$ ..................................................... C07H 21/04
[52] U.S. Cl. .......................................................... 536/23.1
[58] Field of Search ................................. 536/23.1, 24.5; 514/44; 435/240.2, 252.3, 320.1, 325; 530/350

[56] References Cited

U.S. PATENT DOCUMENTS 5,585,479  12/1996  Hoke et al. ............................. 536/24.5

OTHER PUBLICATIONS

Uhlmann et al., Antisense oligonucleotides: a new therapeutic principle, Chemical Reviews, vol. 90(4), pp. 543–584, Jun. 1990.
Gewirtz et al., Facility oligonucleotide delivery: helping antisense deliver on its promise, Proc. Natl. Acad. Sci., vol. 93, pp. 3161–3163, Apr. 1996.
Ngo et al., Computational complexity, protein structure prediction, and the Levinthal paradox, The Protein Folding Problem and Tertiary Structure Prediction, pp. 433–440, 1994.
Chang et al., Identification of herpes–like DNA sequences in AIDS–associated Kaposi's sarcoma, Science, vol. 266 (5192), pp. 1865–1869, Dec. 12, 1994.
Baer et al., "DNA Sequence and Expression of the B95–8 Epstein–Barr Virus Genome," *Nature* 310:207–211 (1984).
Cameron et al., "The 160,000–M$_r$ Virion Protein Encoded at the Right End of the Herpesvirus Saimiri Genome Is Homologous to the 140,000–M$_r$ Membrane Antigen Encoded the Left End of the Epstein–Barr Virus Genome," *Journal of Virology*, 61:2063–2070 (1987).
Albrecht et al., "Primary Structure of the Herpesvirus Saimiri Genome," *Journal of Virology*, 66:5047–5058 (1992).
Nicholas et al., "Herpesvirus Samiri Encodes Homologues of G Protein–Coupled Receptors and Cyclins," *Nature*, 355:362–365 (1992).
Strader et al., "Structure and Function of G Protein–Coupled Receptors," *Annu. Rev. Biochem.*, 63:101–132 (1994).
Ambroziak et al., "Herpes–Like Sequences in HIV–Infected and Uninfected Kaposi's Sarcoma Patients," *Science*, 268:582–583 (1995).
Arvanitakis et al., "Latent Membrane Protein–1 Induces Cyclin D2 Expression, pRb Hyperphosphorylation, and Loss of TGF–β1–Mediated Growth Inhibition in EBV–Positive B Cells," *The Journal of Immunology*, pp. 1047–1056 (1995).

Boshoff et al., "Kaposi's–Sarcoma–Associated Herpesvirus In HIV–Negative Kaposi's Sarcoma," *The Lancet* 345:1043–1044 (1995).
Cesarman et al., "Kaposi's Sarcoma–Associated Herpesvirus–Like DNA Sequences in Aids–Related Body–Cavity––Based Lymphomas," *The New England Journal of Medicine*, 332:1186–1191 (1995).
Cesarman et al., In Vitro Establishment and Characterization of Two Acquired Immunodeficiency Syndrome–Related Lymphoma Cell Lines (BC–1 and BC–2) Containing Kaposi's Sarcoma–Associated Herpesvirus–Like (KSHV) DNA Sequences, *Blood*, 86:2708–271 (1995).
Dupin et al., *New England Journal of Medicine*, p. 798 (1995).
Dupin et al., "Herpesvirus–Like DNA Sequences In Patients With Mediterranean Kaposi's Sarcoma," *The Lancet*, 345:761–762 (1995).
Karcher et al., "Herpes–Like DNA Sequences, Aids–Related Tumors, and Castleman's Disease," *The New England Journal of Medicine*, 333:797–798 (1995).
Moore et al., "Detection of Herpesvirus–Like DNA Sequences in Kaposi's Sarcoma in Patients With and Those Without HIV Infection," *The New England Journal of Medicine*, 332:181–191 (1995).
Noel, "Kaposi's Sarcoma and KSHV," 346:1359–1360 (1995).
Schalling et al, "A Role For A New Herpes Virus (KSHV) In Different Forms of Kaposi's Sarcoma," *Nature Medicine*, 1:707–708 (1995).
Shingadia et al., *The Lancet*, 346:1359–1361 (1995).
Soulier et al., "Kaposi's Sarcoma–Associates Herpesvirus–Like DNA Sequences in Multicentric Castleman's Disease," *Blood*, 86:1276–1280 (1995).
Whitby et al., "Detection of Kaposi Sarcoma–Associated Herpesvirus in Peripheral Blood of HIV–Infected Individuals and Progression to Kaposi's Sarcoma," *The Lancet*, 346:799–802 (1995).
Renne et al., Lytic Growth of Kaposi's Sarcoma–Associated Herpesvirus (Human Herpesvirus 8) in Culture, *Nature Medicine*, 2:342–346 (1996).
Gessain et al., "Kaposi Sarcoma–Associated Herpes–Like Virus (Human Herpesvirus Type 8) DNA Sequences in Multicentric Castleman's Disease: Is There Any Relevant Association In Non–Human Immunodeficiency Virus–Infected Patients?," *Blood*, pp. 414–418 (1996).

*Primary Examiner*—George C. Elliott
*Assistant Examiner*—Andrew Wang
*Attorney, Agent, or Firm*—Nixon Peabody LLP

[57] ABSTRACT

The present invention is directed to isolated nucleic acid molecules encoding proteins of Kaposi's sarcoma associated herpesvirus, including an antigenic receptor protein, a G protein coupled receptor, and a cyclin protein. Expression vectors and host cells comprising the nucleic acid molecules are also provided, as well as methods for increasing or decreasing the expression of the KSHV proteins in host cells. DNA oligomers and antibodies specific for the KSHV proteins are provided, each of which can be used to detect the KSHV proteins in a sample. Isolated KSHV proteins are also provided.

4 Claims, 1 Drawing Sheet

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

AGGAGCGAGA GAGACGGGAT                    20

(2) INFORMATION FOR SEQ ID NO:2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:2:

CCAGGTGCCT GCCCACTTCC                    20

(2) INFORMATION FOR SEQ ID NO:3:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:3:

CCTAGCTCTT GCAGCAGAAC                    20

(2) INFORMATION FOR SEQ ID NO:4:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:4:

CGGGGTGCCT TACACGTGG                                                    19

(2) INFORMATION FOR SEQ ID NO:5:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:5:

CAGTCTGCAG TCATGTTTCC                                                   20

(2) INFORMATION FOR SEQ ID NO:6:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:6:

TGTGTGCGTC AGTCTAGTGA G                                                 21

(2) INFORMATION FOR SEQ ID NO:7:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:7:

GCAGTCTCCA GAGTCTTCTC                                                   20

(2) INFORMATION FOR SEQ ID NO:8:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:8:

CGGAGCTAAA GAGTCTGGTG                                                   20

(2) INFORMATION FOR SEQ ID NO:9:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:9:

TGGAGGTGTA GTCTGCTGCG                                                   20

(2) INFORMATION FOR SEQ ID NO:10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

```
CACCCTGAAA CTCCAGGC                                                    18
```

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

```
GATCCGATCC TCACATAGCG                                                  20
```

(2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

```
CGCCACTCTA TATGCAAACT G                                                21
```

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

```
GGATGTCCAC GTCACACTTC                                                  20
```

(2) INFORMATION FOR SEQ ID NO:14:

(i) SEQUENCE CHARACTERISTICS:
        (A) LENGTH: 4332 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

```
GATCCCGGGA ATTCTCGATC TCGCGGGTTT CTCGGCAGCC TGACTACAGA GGGTGTCCCC       60
GGGGGCGGTG CGCCCTCTAG GCATGGCCTA CGACGTCACT GGGCTGTGGT TGGAGAGTGA      120
TCTCACCGCG GATGAGGAAG CTTTTGTGAA CTTTTATACA AGCCGTACGG GCACACTCAC      180
```

```
TCTCGTACCC GGTGGCACCG GAGGCTACTA TCTGCTATGG ATAACTTTCC GAAGACCTCC    240

CACTTCGAGG GAGGAGCGAG AGAGACGGGA TGTGGAAATA CAGACGGTGC TCGCTGTGCT    300

GTCACCGCTC CTTGGATATC CCCATGTCAT CAGGCGGTCT GTGCCACGGG GGAGCGAGCG    360

TGTTGTATCC TTTGGCTACG GGCCAAACAT GCACCACCGG CCCACAACAT TGTCAACAGA    420

GCTTGCAGTT CTGCTGCAAG AGCTAGGATT GCAGGAGTGG GCTAGAGTGG AAGTGGGCAG    480

GCACCTGGTG TCCAAAATCA CACAGACCCT GCTAGAACCA CACCCACCTC AGTTTATCAG    540

GGCATTTACA CAAAATACCG ACCTGGTACC GTACGAGGGG TTGGAAGTGC CCGAGGGTCC    600

CCAGCCCGTG GCTAGGCCAC ACATTGAAGA TGATGTCATT ATGCAGGCTG TTATGATATC    660

CCTGGGGGGA GACCTGCTAC CGCTGGCGGT GCAGGCTTCA ACCGGGGACA ATTATAACGT    720

GGCCAGGTAC TTTGTGATAC CGGGAAGATG CACCATGGAA CGGTGGCCCT GGAACTGTGC    780

CAGACAGGCG TTCGGGATCC ACGGAGCGTA CACCCACGTC CACAGCAGCG TGCAGAGGGG    840

TATTCGCGGC CTTGGCAACC TGCTGTTTCA CAGCACCCTG TTTCCAGGCG ACAGACACA    900

GGGGCCCTC ACCGGCCTGT ATGCCACCGA ACCGGCCCTG GACCCCGTG CGCACAGCCG    960

ATTCCGTCGC ATATTCGCCA AGGGCGTACA GCAGGCCGAG ATGCTGCAGG GAGCGGGAGT   1020

CCCCACCCTG GGGGGTTTCT TAAAAACGGT GCGCACCATC GCCACCACTC CTGGCAACGC   1080

CCTGGCAGTC TGCTCCATCT CTACCACTAC TTCCAAAGAA TGCATCTCCC TGAGAAGGAT   1140

GATCCCCCAG CAGACAGTGG TGTGTCTGGG CAGGTTTGAG CCCACGGATG GACCGGACAC   1200

CTACCCTAAC CTCTATCGCG ACAGCTCCGA CAATGCGGTG CGCATCTTGG AGACCCTGAA   1260

GCTGGTCCAG CGGCTTGCCA AGGGCCCTAT CTTCTCCGGA CTAAACAGAT CGCATGACCC   1320

GGCCCCGGTG GTGAGGCACC TGCAGGCGCT GGCGCCGCGG ACCGGCCTGG AGCTGTTTGT   1380

CTCCAAGCTA CCCGACGAGG TGCGCACCCA CCTGCCTGCG GATCCCGCGG CCGGTCCGGA   1440

TGCCGTGAAG GCGGCGGTGG CAGAGCACTT TCTCAACGTG TATTGCTCCC TGGTGTTTGC   1500

GGTGGTGGCA GAGTCGGGCG CGGTGCCTGG GGATCTGGGC GAGACCCCGT TGGAGGTACT   1560

GCAGCGCGCC GCGCGCCTGT GCGCGTGCCA GGTAACGGTC CTCGGGAGGA CCTCGGAGCA   1620

CCCAGGCATC AGAATAGTAG ACGACCTGAC CGGGGAGACC ACGAGGGTCT TCTCTGTAGA   1680

CCAGCCGTCG TCCACCCCCC CGTCCCCCTG GCTGGCGCTG TCCGATGGTG TCCGCGTCTC   1740

GGGGCACCCC GAGGATGTTG ACTGGGGCCT TTTTGCCACC GGCTCCACAA TCCACCAGTT   1800

ACTTCGCCAC TCGACGGTTG GCAGCAAGGA GTTCTTTACG CGACACATGG ACCGATGCTC   1860

CAACGGCCTC ATCGCCCAAC AGGCTGGCGT GGGACCCCTG GACATACCGG TTTCAGACTA   1920

CCACCTGGTG CTGCACTCGT CCATGCTGGC CGAGAGGGTG GCGCCCAGAG TGCCCGACAC   1980

GGTGGAGGCC ATCACTCCGT CCATGGCCAA CCTCCTACAC AAGGACTTCG AGACCTGGGT   2040

GAAGGCCCTG CCCCAGGAGC TGCTTCCAGT GCCAGCGTGG AGGGGTCAGG CAATGGCCAT   2100

GGGGGAGCAG GCCTACAAGA TGGCTACTAA TGTATCCACC GGGGCCACCT ATGCCATCAC   2160

CGAGGCTCTC ACCAACCTCA TGTTCAGTCC CGTGTCCAAG CTCCAGGACG TAGTGCTAAC   2220

TGGCGCCGTG GCGTGGAGTC CAGAGGACCA CCAAGCCGGC CTCCTACAGG AGTGCCTCTT   2280

CGCCTGCAAG GAATTCTGCC GGGAGCTGGG AGTGGCACTG TCCATCTCCT CGGCTGCCAG   2340

CTCTCCGACG CTTTCGGAGC GCCATGTGCG CATCACACAA CAGCAAGAAA CGGTGGAGGT   2400

CCTTCCCTTC AACTCGGTGG TGTTTACCAG CTGGGCCGAG GTCAAGGGAT CCAGATACAG   2460

GGTCACCCCG GACGTAAAGG TCGAAGGCAA CGCCCTGGTA TACCTGGCCG TGAATCAGAG   2520
```

-continued

```
CTGTCTCATA GCCGGGTCCA CCTTCGAGCA CAACTTCCTG GCATCCAGGC ACCCAATACC    2580

CCCTCTGAAC CCGTCCACGG TCGCCAGCCT GTTCATGCTT GTTAAGTACC TGATGTCCAA    2640

GAGGCTCATT GTATCTGGGC ACGACATAGG GGACGGAGGG CTTCTCCCAT CTGCAATCGA    2700

GATGGCCCTG GCCGGCTGCA GGGGACTGCA GCTCTCACTA CCCGCCCACC CTAACCCGCT    2760

CGAACTTATG GTTTCAGAGA CCCCTGGGGC ACTGGTTGAG GTGCCCCAGG TACACTTGTC    2820

AGAGGTGCTG CGGGCGGCCA GGGACTACCG CTGCGTGGCA CACCCACTGG GCACCGTTGG    2880

CCCCGAGGGA CAAGGCAACA ACGTCACGGT TTTGCAGAAC GAGACAGTTG TGTTTCAAGA    2940

GACCCTGACT TCCTTGCAAG TCTCATGGAC CTCCTTTTCT GACGAAATGT GGAACCTGGT    3000

GACGCCTCCC CTGCACCCAC TGGAGGACAT GCACAGGAAG GACCTGGGTC GTCTGGAGCA    3060

TCACCTGGGC AGCCTAAGGG CCATGTGCCT TGGGAGTCAG CTGCGCCTGT TTTCGTGCCC    3120

CACCTCCCCG CGCCGTGTGG CCGCGTTGGT GCTGCCTGGG AGCAGTGCCC CGTACGCGCT    3180

CATGGCCGCG TTGCAGAACA CGGGCTTTGA GGTGGCCACG GTGACTGTGG AAGAGCTTAA    3240

ACGAGGACAG TCCTTGTCGG GGTTCTCTGG TCTGATTACA TGTCTCAGAA CAGGCTGCCA    3300

GGCCAGCTAC GCCAGCGCCA GGGGATGGGT CCTGGCGCTG TGTAACGACC CTACCTGTGC    3360

CTCCACCCTG ACAGAGTTTC TAAACAGACC CGACACATTC TCCATCTGCT GTGGCGAGGT    3420

GGGCTTCCAG CTGCTGGTGG CCCTGGGTGT AGTGGGCCGG TCGGAATCCT CACCATACAC    3480

GTACGGACCC ACACCACCCC AGCGCTGGGC GGTAAACCTG GAGACCAACG TGTCCAAGCT    3540

GTATGACAGC CACTGGCTAA ACATACAGAT CCCTCAGAAC ACTAAGAGCG TTTTCCTCCG    3600

AGTGTTGCGG GGGACGGTGC TGCCCAGCTG GGCCCAGGGA GAGTACCTGG GGGTCCGGTA    3660

CGAGCAGGAC GCCCTCGAGT ACATACTGAG ACAGCGAGGC GAGATAACCC TCACCTACCA    3720

TGGAAATGCC GCGGATGAGA CCCTGCCAGC CAGACACTAT CCCAGAAACC CCACAGGCAA    3780

CTCCACGGTG GCCGGACTTA CATCCAGTGA CGGGCGACAC GCTGCCCTGA TCATAGACCC    3840

ATCTCTGATG TTCCATCCGT GGCAGTGGCA GCATGTTCCA CCAGACCTAA CACCCCTGTC    3900

CATGTCCCCG TGGGCCATGG CGTTCCAGTC AATCTACCTA TGGAGCGTCA AGAAGATCAA    3960

CGACCACCAC TAAACATTGC TTTTGGGATC AGACCCCTCA TTTAATCGCA TAATAAAACA    4020

AATACATAGT CACATCTGTG TACAAACCAA ATTCGCCTCT CTGCATCATG GAACGGGAG    4080

GCTAGATTAA ATTAAGGGGG AAGGGCACGT AGACATCCGC GGGCTACGTG GTGGCGCCGG    4140

ACATGAAAGA CTGCCTGAGG CTTTGGAAGA GACCGTACAT CCTCTGCCTA AGAGGGATC    4200

CCAGGCAGGA GTATATCAGG GGAACCACGG CGCTGTACAG TGCCTGCAGT AACGAGGTTA    4260

CTGCCAGACC CACGTTTATC AACCCCCGCG TATAGCAGCT GTCCCGGATC CAGCGTCGCC    4320

TTAGCAGAGT GT                                                       4332
```

(2) INFORMATION FOR SEQ ID NO:15:

(i) SEQUENCE CHARACTERISTICS:
        (A) LENGTH: 1296 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:15:

```
Met Ala Tyr Asp Val Thr Gly Leu Trp Leu Glu Ser Asp Leu Thr Ala
1               5                   10                  15

Asp Glu Glu Ala Phe Val Asn Phe Tyr Thr Ser Arg Thr Gly Thr Leu
```

```
                    20                  25                  30
Thr Leu Val Pro Gly Thr Gly Tyr Tyr Leu Leu Trp Ile Thr
        35                  40                  45

Phe Arg Arg Pro Pro Thr Ser Arg Glu Glu Arg Glu Arg Asp Val
50                      55                  60

Glu Ile Gln Thr Val Leu Ala Val Leu Ser Pro Leu Leu Gly Tyr Pro
65                      70                  75                  80

His Val Ile Arg Arg Ser Val Pro Arg Gly Ser Glu Arg Val Val Ser
                    85                  90                  95

Phe Gly Tyr Gly Pro Asn Met His His Arg Pro Thr Thr Leu Ser Thr
                100                 105                 110

Glu Leu Ala Val Leu Leu Gln Glu Leu Gly Leu Gln Glu Trp Ala Arg
                115                 120                 125

Val Glu Val Gly Arg His Leu Val Ser Lys Ile Thr Gln Thr Leu Leu
                130                 135                 140

Glu Pro His Pro Pro Gln Phe Ile Arg Ala Phe Thr Gln Asn Thr Asp
145                 150                 155                 160

Leu Val Pro Tyr Glu Gly Leu Glu Val Pro Glu Gly Pro Gln Pro Val
                165                 170                 175

Ala Arg Pro His Ile Glu Asp Asp Val Ile Met Gln Ala Val Met Ile
                180                 185                 190

Ser Leu Gly Ala Asp Leu Leu Pro Leu Ala Val Gln Ala Ser Thr Gly
                195                 200                 205

Asp Asn Tyr Asn Val Ala Arg Tyr Phe Val Ile Pro Gly Arg Cys Thr
                210                 215                 220

Met Glu Arg Trp Pro Trp Asn Cys Ala Arg Gln Ala Phe Gly Ile His
225                 230                 235                 240

Gly Ala Tyr Thr His Val His Ser Ser Val Gln Arg Gly Ile Arg Gly
                245                 250                 255

Leu Gly Asn Leu Leu Phe His Ser Thr Leu Phe Pro Gly Gly Gln Thr
                260                 265                 270

Gln Gly Ala Leu Thr Gly Leu Tyr Ala Thr Glu Pro Ala Leu Gly Pro
                275                 280                 285

Arg Ala His Ser Arg Phe Arg Arg Ile Phe Ala Lys Gly Val Gln Gln
                290                 295                 300

Ala Glu Met Leu Gln Gly Ala Val Pro Thr Leu Gly Gly Phe Leu
305                 310                 315                 320

Lys Thr Val Arg Thr Ile Ala Thr Thr Pro Gly Asn Ala Leu Ala Val
                325                 330                 335

Cys Ser Ile Ser Thr Thr Thr Ser Lys Glu Cys Ile Ser Leu Arg Arg
                340                 345                 350

Met Ile Pro Gln Gln Thr Val Val Cys Leu Gly Arg Phe Glu Pro Thr
                355                 360                 365

Asp Gly Pro Asp Thr Tyr Pro Asn Leu Tyr Arg Asp Ser Ser Asp Asn
370                 375                 380

Ala Val Arg Ile Leu Glu Thr Leu Lys Leu Val Gln Arg Leu Ala Lys
385                 390                 395                 400

Gly Pro Ile Phe Ser Gly Leu Asn Arg Ser His Asp Pro Ala Pro Val
                405                 410                 415

Val Arg His Leu Gln Ala Leu Ala Pro Arg Thr Gly Leu Glu Leu Phe
                420                 425                 430

Val Ser Lys Leu Pro Asp Glu Val Arg Thr His Leu Pro Ala Asp Pro
435                 440                 445
```

```
Ala Ala Gly Pro Asp Ala Val Lys Ala Ala Val Ala Glu His Phe Leu
    450                 455                 460
Asn Val Tyr Cys Ser Leu Val Phe Ala Val Ala Glu Ser Gly Ala
465                 470                 475                 480
Val Pro Gly Asp Leu Gly Glu Thr Pro Leu Glu Val Leu Gln Arg Ala
            485                 490                 495
Ala Arg Leu Cys Ala Cys Gln Val Thr Val Leu Gly Arg Thr Ser Glu
                500                 505                 510
His Pro Gly Ile Arg Ile Val Asp Asp Leu Thr Gly Thr Thr Arg
            515                 520                 525
Val Phe Ser Val Asp Gln Pro Ser Ser Thr Pro Pro Ser Pro Trp Leu
    530                 535                 540
Ala Leu Ser Asp Gly Val Arg Val Ser Gly His Pro Glu Asp Val Asp
545                 550                 555                 560
Trp Gly Leu Phe Ala Thr Gly Ser Thr Ile His Gln Leu Leu Arg His
                565                 570                 575
Ser Thr Val Gly Ser Lys Glu Phe Phe Thr Arg His Met Asp Arg Cys
            580                 585                 590
Ser Asn Gly Leu Ile Ala Gln Gln Ala Gly Val Gly Pro Leu Asp Ile
            595                 600                 605
Pro Val Ser Asp Tyr His Leu Val Leu His Ser Ser Met Leu Ala Glu
    610                 615                 620
Arg Val Ala Pro Arg Val Pro Asp Thr Val Glu Ala Ile Thr Pro Ser
625                 630                 635                 640
Met Ala Asn Leu Leu His Lys Asp Phe Glu Thr Trp Val Lys Ala Leu
                645                 650                 655
Pro Gln Glu Leu Leu Pro Val Pro Ala Trp Arg Gly Gln Ala Met Ala
            660                 665                 670
Met Gly Glu Gln Ala Tyr Lys Met Ala Thr Asn Val Ser Thr Gly Ala
            675                 680                 685
Thr Tyr Ala Ile Thr Glu Ala Leu Thr Asn Leu Met Phe Ser Pro Val
    690                 695                 700
Ser Lys Leu Gln Asp Val Val Leu Thr Gly Ala Val Ala Trp Ser Pro
705                 710                 715                 720
Glu Asp His Gln Ala Gly Leu Leu Gln Glu Cys Leu Phe Ala Cys Lys
                725                 730                 735
Glu Phe Cys Arg Glu Leu Gly Val Ala Leu Ser Ile Ser Ser Ala Ala
            740                 745                 750
Ser Ser Pro Thr Leu Ser Glu Arg His Val Arg Ile Thr Gln Gln Gln
            755                 760                 765
Glu Thr Val Glu Val Leu Pro Phe Asn Ser Val Phe Thr Ser Trp
    770                 775                 780
Ala Glu Val Lys Gly Ser Arg Tyr Arg Val Thr Pro Asp Val Lys Val
785                 790                 795                 800
Glu Gly Asn Ala Leu Val Tyr Leu Ala Val Asn Gln Ser Cys Leu Ile
                805                 810                 815
Ala Gly Ser Thr Phe Glu His Asn Phe Leu Ala Ser Arg His Pro Ile
            820                 825                 830
Pro Pro Leu Asn Pro Ser Thr Val Ala Ser Leu Phe Met Leu Val Lys
            835                 840                 845
Tyr Leu Met Ser Lys Arg Leu Ile Val Ser Gly His Asp Ile Gly Asp
    850                 855                 860
```

-continued

```
Gly Gly Leu Leu Pro Ser Ala Ile Glu Met Ala Leu Ala Gly Cys Arg
865                 870                 875                 880

Gly Leu Gln Leu Ser Leu Pro Ala His Pro Asn Pro Leu Glu Leu Met
            885                 890                 895

Val Ser Glu Thr Pro Gly Ala Leu Val Glu Val Pro Gln Val His Leu
        900                 905                 910

Ser Glu Val Leu Arg Ala Ala Arg Asp Tyr Arg Cys Val Ala His Pro
    915                 920                 925

Leu Gly Thr Val Gly Pro Glu Gly Gln Gly Asn Asn Val Thr Val Leu
930                 935                 940

Gln Asn Glu Thr Val Val Phe Gln Glu Thr Leu Thr Ser Leu Gln Val
945                 950                 955                 960

Ser Trp Thr Ser Phe Ser Asp Glu Met Trp Asn Leu Val Thr Pro Pro
            965                 970                 975

Leu His Pro Leu Glu Asp Met His Arg Lys Asp Leu Gly Arg Leu Glu
        980                 985                 990

His His Leu Gly Ser Leu Arg Ala Met Cys Leu Gly Ser Gln Leu Arg
    995                 1000                1005

Leu Phe Ser Cys Pro Thr Ser Pro Arg Arg Val Ala Ala Leu Val Leu
    1010                1015                1020

Pro Gly Ser Ser Ala Pro Tyr Ala Leu Met Ala Ala Leu Gln Asn Thr
1025                1030                1035                1040

Gly Phe Glu Val Ala Thr Val Thr Val Glu Glu Leu Lys Arg Gly Gln
            1045                1050                1055

Ser Leu Ser Gly Phe Ser Gly Leu Ile Thr Cys Leu Arg Thr Gly Cys
            1060                1065                1070

Gln Ala Ser Tyr Ala Ser Ala Arg Gly Trp Val Leu Ala Leu Cys Asn
        1075                1080                1085

Asp Pro Thr Cys Ala Ser Thr Leu Thr Glu Phe Leu Asn Arg Pro Asp
    1090                1095                1100

Thr Phe Ser Ile Cys Cys Gly Glu Val Gly Phe Gln Leu Leu Val Ala
1105                1110                1115                1120

Leu Gly Val Val Gly Arg Ser Glu Ser Ser Pro Tyr Thr Tyr Gly Pro
            1125                1130                1135

Thr Pro Pro Gln Arg Trp Ala Val Asn Leu Glu Thr Asn Val Ser Lys
            1140                1145                1150

Leu Tyr Asp Ser His Trp Leu Asn Ile Gln Ile Pro Gln Asn Thr Lys
        1155                1160                1165

Ser Val Phe Leu Arg Val Leu Arg Gly Thr Val Leu Pro Ser Trp Ala
    1170                1175                1180

Gln Gly Glu Tyr Leu Gly Val Arg Tyr Glu Gln Asp Ala Leu Glu Tyr
1185                1190                1195                1200

Ile Leu Arg Gln Arg Gly Glu Ile Thr Leu Thr Tyr His Gly Asn Ala
            1205                1210                1215

Ala Asp Glu Thr Leu Pro Ala Arg His Tyr Pro Arg Asn Pro Thr Gly
            1220                1225                1230

Asn Ser Thr Val Ala Gly Leu Thr Ser Ser Asp Gly Arg His Ala Ala
        1235                1240                1245

Leu Ile Ile Asp Pro Ser Leu Met Phe His Pro Trp Gln Trp Gln His
    1250                1255                1260

Val Pro Pro Asp Leu Thr Pro Leu Ser Met Ser Pro Trp Ala Met Ala
1265                1270                1275                1280

Phe Gln Ser Ile Tyr Leu Trp Ser Val Lys Lys Ile Asn Asp His His
```

(2) INFORMATION FOR SEQ ID NO:16:

(i) SEQUENCE CHARACTERISTICS:
        (A) LENGTH: 1202 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

```
AAAAGGCGTG GCTAAACAAC ACCTATACTA CTTGTTATTG TAGGCCATGG CGGCCGAGGA      60
TTTCCTAACC ATCTTCTTAG ATGATGATGA ATCCTGGAAT GAAACTCTAA ATATGAGCGG     120
ATATGACTAC TCTGGAAACT TCAGCCTAGA AGTGAGCGTG TGTGAGATGA CCACCGTGGT     180
GCCTTACACG TGGAACGTTG AATACTCTC TCTGATTTTC CTCATAAATG TTCTTGGAAA      240
TGGATTGGTC ACCTACATTT TTTGCAAGCA CCGATCGCGG GCAGGAGCGA TAGATATACT     300
GCTCCTGGGT ATCTGCCTAA ACTCGCTGTG TCTTAGCATA TCTCTATTGG CAGAAGTGTT     360
GATGTTTTTG TTTCCCAATA TCATCTCCAC AGGCTTGTGC AGACTTGAAA TTTTTTTTTA     420
CTATTTATAT GTCTACTTGG ATATCTTCAG TGTTGTGTGC GTCAGTCTAG TGAGGTACCT     480
CCTGGTGGCA TATTCTACGC GTTCCTGGCC CAAGAAGCAG TCCCTCGGAT GGGTACTGAC     540
ATCCGCTGCA CTGTTAATTG CATTGGTGCT GTCGGGGGAT GCCTGTCGAC ACAGGAGCAG     600
GGTGGTCGAC CCGGTCAGCA AGCAGGCCAT GTGTTATGAG AACGCGGGAA ACATGACTGC     660
AGACTGGCGA CTGCATGTCA GAACCGTGTC AGTTACTGCA GGTTTCCTGT TACCCCTGGC     720
CCTCCTTATT CTGTTTTATG CTCTCACCTG GTGTGTGGTG AGGAGGACAA AGCTGCAAGC     780
CAGGCGGAAG GTAAGGGGGG TGATTGTTGC TGTGGTGCTG CTGTTTTTTG TGTTTTGCTT     840
CCCTTACCAC GTACTAAATC TACTGGACAC TCTGCTAAGG CGACGCTGGA TCCGGGACAG     900
CTGCTATACG CGGGGGTTGA TAAACGTGGG TCTGGCAGTA ACCTCGTTAC TGCAGGCACT     960
GTACAGCGCC GTGGTTCCCC TGATATACTC CTGCCTGGGA TCCCTCTTTA GGCAGAGGAT    1020
GTACGGTCTC TTCCAAAGCC TCAGGCAGTC TTTCATGTCC GGCGCCACCA CGTAGCCCGC    1080
GGATGTCTAC GTGCCCTTCC CCCTTAATTT AATCTAGCCT CCCGTTCCCA TGATGCAGAG    1140
AGGCGAATTT GGTTTGTACA CAGATGTGAC TATGTATTTG TTTTATTATG CGATTAAATG    1200
AG                                                                  1202
```

(2) INFORMATION FOR SEQ ID NO:17:

(i) SEQUENCE CHARACTERISTICS:
        (A) LENGTH: 342 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:17:

```
Met Ala Ala Glu Asp Phe Leu Thr Ile Phe Leu Asp Asp Asp Glu Ser
1               5                  10                  15

Trp Asn Glu Thr Leu Asn Met Ser Gly Tyr Asp Tyr Ser Gly Asn Phe
            20                  25                  30

Ser Leu Glu Val Ser Val Cys Glu Met Thr Thr Val Val Pro Tyr Thr
        35                  40                  45
```

```
Trp Asn Val Gly Ile Leu Ser Leu Ile Phe Leu Ile Asn Val Leu Gly
 50                  55                  60

Asn Gly Leu Val Thr Tyr Ile Phe Cys Lys His Arg Ser Arg Ala Gly
 65                  70                  75                  80

Ala Ile Asp Ile Leu Leu Gly Ile Cys Leu Asn Ser Leu Cys Leu
                 85                  90                  95

Ser Ile Ser Leu Leu Ala Glu Val Leu Met Phe Leu Phe Pro Asn Ile
            100                 105                 110

Ile Ser Thr Gly Leu Cys Arg Leu Glu Ile Phe Phe Tyr Tyr Leu Tyr
            115                 120                 125

Val Tyr Leu Asp Ile Phe Ser Val Val Cys Val Ser Leu Val Arg Tyr
            130                 135                 140

Leu Leu Val Ala Tyr Ser Thr Arg Ser Trp Pro Lys Lys Gln Ser Leu
145                 150                 155                 160

Gly Trp Val Leu Thr Ser Ala Ala Leu Leu Ile Ala Leu Val Leu Ser
                165                 170                 175

Gly Asp Ala Cys Arg His Arg Ser Arg Val Val Asp Pro Val Ser Lys
                180                 185                 190

Gln Ala Met Cys Tyr Glu Asn Ala Gly Asn Met Thr Ala Asp Trp Arg
            195                 200                 205

Leu His Val Arg Thr Val Ser Val Thr Ala Gly Phe Leu Leu Pro Leu
            210                 215                 220

Ala Leu Leu Ile Leu Phe Tyr Ala Leu Thr Trp Cys Val Val Arg Arg
225                 230                 235                 240

Thr Lys Leu Gln Ala Arg Arg Lys Val Arg Gly Val Ile Val Ala Val
                245                 250                 255

Val Leu Leu Phe Phe Val Phe Cys Phe Pro Tyr His Val Leu Asn Leu
                260                 265                 270

Leu Asp Thr Leu Leu Arg Arg Arg Trp Ile Arg Asp Ser Cys Tyr Thr
            275                 280                 285

Arg Gly Leu Ile Asn Val Gly Leu Ala Val Thr Ser Leu Leu Gln Ala
            290                 295                 300

Leu Tyr Ser Ala Val Val Pro Leu Ile Tyr Ser Cys Leu Gly Ser Leu
305                 310                 315                 320

Phe Arg Gln Arg Met Tyr Gly Leu Phe Gln Ser Leu Arg Gln Ser Phe
                325                 330                 335

Met Ser Gly Ala Thr Thr
            340
```

(2) INFORMATION FOR SEQ ID NO:18:

(i) SEQUENCE CHARACTERISTICS:
    (A) LENGTH: 863 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:18:

```
GAGAACCTGA CAGAGCACCC TGAAACTCCA GGCTCTACAG GTAGGCCACA TACGCTCGCC    60

ACTCTATATG GCAACTGCCA ATAACCCGCC CTCGGGACTT CTGGATCCCA CGCTATGTGA   120

GGATCGGATC TTTTACAATA TTCTTGAAAT TGAGCCGCGC TTTTTAACTT CTGACTCTGT   180

ATTTGGGACC TTTCAACAAT CTCTTACTTC GCATATGCGT AAGTTACTGG GCACATGGAT   240

GTTTTCAGTT TGCCAGGAAT ACAACCTAGA ACCTAACGTG GTCGCGTTGG CCCTTAATCT   300
```

```
TTTGGACAGA CTCCTACTTA TAAAGCAGGT GTCCAAAGAA CACTTTCAAA AGACAGGGAG      360

CGCCTGCCTG TTAGTGGCCA GTAAGCTCAG AAGCCTCACG CCTATTTCTA CCAGTTCACT      420

TTGCTATGCC GCGGCAGACT CCTTTTCCCG CCAAGAACTT ATAGACCAGG AGAAAGAACT      480

CCTTGAGAAG TTGGCGTGGC GAACAGAGGC AGTCTTAGCG ACGGACGTCA CTTCCTTCTT      540

GTTACTTAAA TTGCTGGGGG GCTCCCAACA CCTGGACTTT TGGCACCACG AGGTCAACAC      600

CCTGATTACA AAAGCCTTAG TTGACCCAAA GACTGGCTCA TTGCCCGCCT CTATTATCAG      660

CGCTGCAGGC TGTGCGCTGT TGGTTCCTGC AACGTCATT CCGCAGGATA CCCACTCGGG       720

TGGGGTAGTT CCTCAGCTGG CAAGCATATT GGGATGCGAT GTTTCCGTTC TACAGGCGGC      780

AGTGGAACAG ATCCTAACAT CTGTTTCGGA CTTTGATCTG CGCATTCTGG ACAGCTATTA      840

AGCTTGTGAT TTTGTTTAGG GCG                                             863
```

(2) INFORMATION FOR SEQ ID NO:19:

(i) SEQUENCE CHARACTERISTICS:
        (A) LENGTH: 257 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:19:

```
Met Ala Thr Ala Asn Asn Pro Pro Ser Gly Leu Leu Asp Pro Thr Leu
1               5                   10                  15

Cys Glu Asp Arg Ile Phe Tyr Asn Ile Leu Glu Ile Glu Pro Arg Phe
            20                  25                  30

Leu Thr Ser Asp Ser Val Phe Gly Thr Phe Gln Gln Ser Leu Thr Ser
        35                  40                  45

His Met Arg Lys Leu Leu Gly Thr Trp Met Phe Ser Val Cys Gln Glu
    50                  55                  60

Tyr Asn Leu Glu Pro Asn Val Val Ala Leu Ala Leu Asn Leu Leu Asp
65                  70                  75                  80

Arg Leu Leu Leu Ile Lys Gln Val Ser Lys Glu His Phe Gln Lys Thr
                85                  90                  95

Gly Ser Ala Cys Leu Leu Val Ala Ser Lys Leu Arg Ser Leu Thr Pro
            100                 105                 110

Ile Ser Thr Ser Ser Leu Cys Tyr Ala Ala Ala Asp Ser Phe Ser Arg
        115                 120                 125

Gln Glu Leu Ile Asp Gln Glu Lys Glu Leu Leu Glu Lys Leu Ala Trp
    130                 135                 140

Arg Thr Glu Ala Val Leu Ala Thr Asp Val Thr Ser Phe Leu Leu Leu
145                 150                 155                 160

Lys Leu Leu Gly Gly Ser Gln His Leu Asp Phe Trp His His Glu Val
                165                 170                 175

Asn Thr Leu Ile Thr Lys Ala Leu Val Asp Pro Lys Thr Gly Ser Leu
            180                 185                 190

Pro Ala Ser Ile Ile Ser Ala Ala Gly Cys Ala Leu Leu Val Pro Ala
```

```
                195                 200                 205
Asn Val Ile Pro Gln Asp Thr His Ser Gly Gly Val Val Pro Gln Leu
    210                 215                 220

Ala Ser Ile Leu Gly Cys Asp Val Ser Val Leu Gln Ala Ala Val Glu
225                 230                 235                 240

Gln Ile Leu Thr Ser Val Ser Asp Phe Asp Leu Arg Ile Leu Asp Ser
                245                 250                 255

Tyr
```

DNA ENCODING PROTEINS OF KAPOSI'S SARCOMA ASSOCIATED HERPESVIRUS

The subject matter of this application was made with support from the United States Government under National Institutes of Health Grant Nos. CA68939 and EY06337.

FIELD OF THE INVENTION

The present invention relates generally to proteins of Kaposi's sarcoma associated herpesvirus and, more particularly, to an antigenic membrane protein, a G protein coupled receptor, and a cyclin protein of Kaposi's sarcoma-associated herpesvirus, nucleic acid molecules encoding the proteins, and uses thereof.

BACKGROUND OF THE INVENTION

Throughout this application various publications are referenced, many in parenthesis. Full citations for these publications are provided at the end of the Detailed Description of the Invention. The disclosures of these publications in their entireties are hereby incorporated by reference in this application.

Two novel DNA fragments belonging to a previously unidentified human herpesvirus were recently identified in a Kaposi's sarcoma (KS) lesion (Chang et al. 1994). Extensive sequencing, transmission and serologic studies demonstrate that these sequences belong to a new human herpesvirus, Kaposi's sarcoma-associated herpesvirus (KSHV), also called human herpesvirus 8 (HHV 8) (Moore et al. 1996a). While this virus is generally absent from normal control tissues, it is consistently present in AIDS- and non-AIDS-related KS (Boshoff et al. 1995; Chang et al. 1994; Chang et al. 1996; Dupin et al. 1995b; Moore and Chang 1995; Schalling et al. 1995), AIDS- and non-AIDS-related primary effusion (body cavity-based) lymphomas (Cesarman et al. 1995a; Karcher and Alkan 1995), and a significant proportion of cases of multicentric Castleman's disease (Dupin et al. 1995a; Gessain et al. 1995; Soulier et al. 1995). These sequences are also frequently present in normal appearing tissue adjacent to KS lesions, and in lymph nodes and peripheral blood B cells in patients with KS or at high risk for developing KS (Ambroziak et al. 1995; Chang et al. 1994; Moore et al. 1996b; Noel 1995; Shigandia et al. 1995; Whitby et al. 1995).

Detection of KSHV in lymph nodes, peripheral blood B-cells, and a subset of B-cell lymphomas suggests that it is a lymphotropic herpesvirus. The initial sequence analysis data showing partial homology to Herpesvirus saimiri (HVS) and Epstein-Barr virus (EBV) is consistent with this hypothesis (Chang et al. 1994). Both viruses are members of the Gammaherpesvirinae subfamily of herpesviruses, which characteristically replicate in lymphoblastoid cells. HVS, a squirrel monkey virus (Saimiri scireus), can be isolated from the peripheral blood mononuclear cells of healthy animals, but causes fulminant T-cell lymphomas in New World primates other than its natural hosts (Fleckenstein and Desrosiers 1982). HVS can also immortalize human T cells so that they grow continuously in vitro (Biesinger et al. 1992). EBV is a human herpesvirus well known to immortalize B cells in vitro and is associated with malignant lymphomas, including endemic Burkitt's lymphoma, AIDS-related lymphomas, post-transplantation lymphoproliferative disorders, and Hodgkin's disease (Miller 1990). Since both viruses can lead to the development of malignant lymphomas, it is quite possible that KSHV is a transforming virus which is involved in the development of primary effusion lymphomas.

Since the original identification of two small DNA fragments from an AIDS-KS lesion by representational difference analysis, considerable progress has been made in determining the nature of this virus. Cell lines have been established which allow the in vitro culture of the virus and detailed virologic characterization studies (Arvanitakis et al. 1996; Cesarman et al. 1995b). A 20.7 kb clone from a KS library has been sequenced and characterized, confirming that KSHV is a gamma-2 herpesvirus, the first member of the genus Rhadinovirus known to infect humans (Moore et al. 1996a). In vitro transmission and visualization at the electron microscopic level have also been achieved, providing additional evidence for the viral nature of the KSHV sequences (Mesri et al. 1996; Moore et al. 1996a; Renne et al. 1996; Said et al. 1996).

A need continues to exist for more information about KSHV, including the identification and/or sequencing of proteins of this virus. Such proteins, when identified and sequenced, could be used in many ways.

SUMMARY OF THE INVENTION

The present invention provides the identification and/or sequencing of three such proteins of KSHV. The first protein is an antigenic membrane protein; the second protein is a G protein coupled receptor; and the third protein is a cyclin protein. The invention thus provides isolated nucleic acid molecules encoding these three proteins of Kaposi's sarcoma-associated herpesvirus, as well as antisense molecules and ribozymes derived therefrom.

The isolated nucleic acid molecules of the invention can be inserted into suitable expression vectors and/or host cells. Expression of a nucleic acid molecule encoding one of the proteins of KSHV results in production of the protein in a host cell. Expression of the antisense nucleic acid molecules in a host cell or introduction of the ribozymes into a host cell results in decreased expression of the protein.

Further provided are isolated nucleic acid molecules encoding such proteins, wherein each nucleic acid molecule encodes a first amino acid sequence having at least 90% amino acid identity to a second amino acid sequence. The second amino acid sequence is, in preferred embodiments, SEQ ID NO:15, 17, or 19.

The invention further provides a DNA oligomer capable of hybridizing to a nucleic acid molecule encoding a protein of KSHV. The DNA oligomer can be used in a method of detecting presence of a nucleic acid molecule encoding a protein of KSHV in a sample, which method is also provided by the subject invention.

The invention further provides these three isolated proteins of KSHV, as well as antibodies or fragments thereof specific for each protein. The antibodies or fragments thereof can also be used in methods of detecting the presence of the proteins of KSHV in a sample, which method is also provided by the subject invention.

Also provided are such isolated proteins, wherein each isolated protein is encoded by a first amino acid sequence have at least 90% amino acid identity to a second amino acid sequence. The second amino acid sequence is, in preferred embodiments, SEQ ID NO:15, 17, or 19.

The invention further provides a method for detecting infection of a cell by KSHV. The method comprises detecting the presence of one or more of the three proteins provided herein in a cell, which can be accomplished using antibodies or fragments thereof, or using DNA oligomers, as also provided herein.

BRIEF DESCRIPTION OF THE DRAWINGS

These and other features and advantages of this invention will be evident from the following detailed description of preferred embodiments when read in conjunction with the accompanying drawings in which.

DETAILED DESCRIPTION OF THE INVENTION

Figures 1, 2:
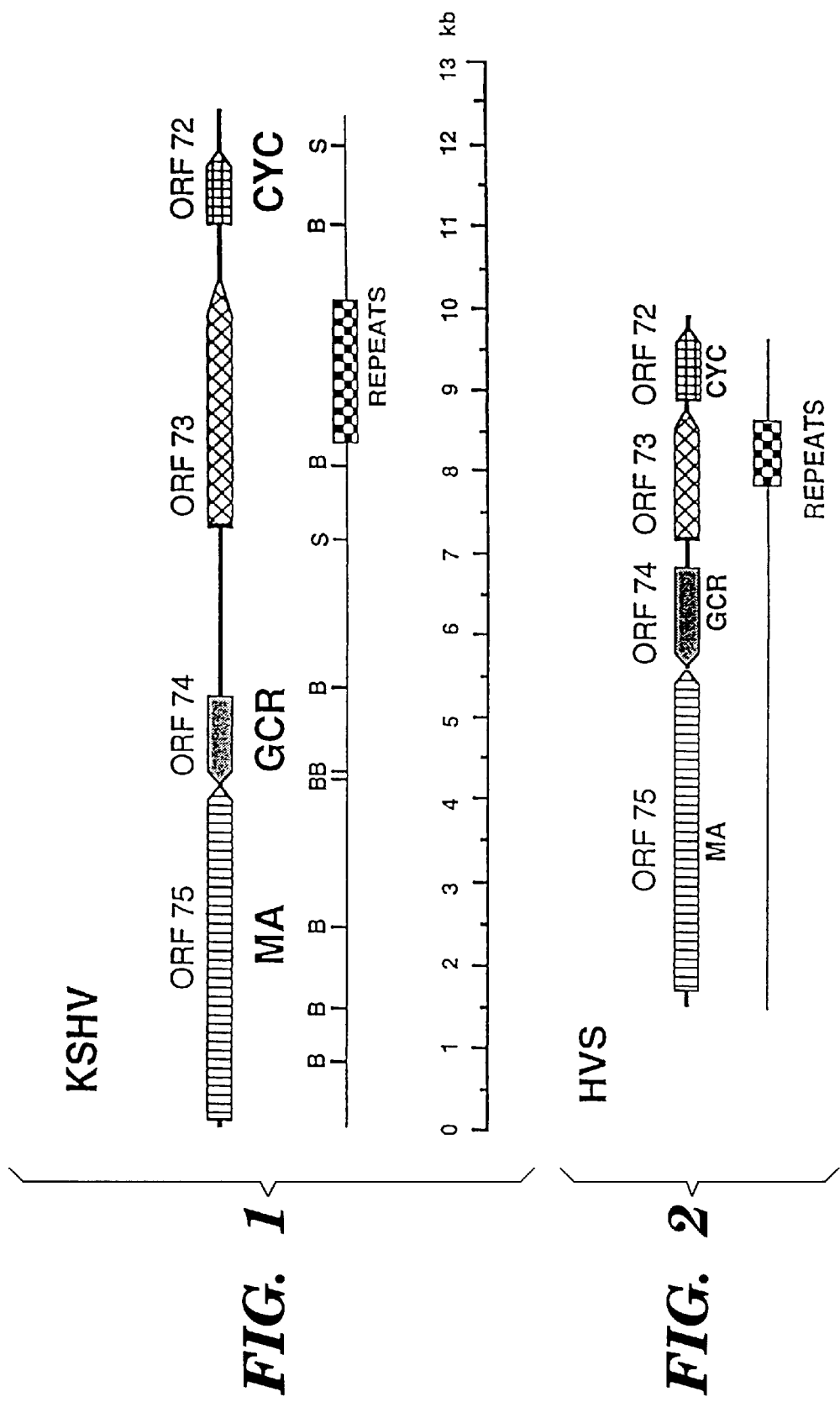
FIG. 1 shows the general structure of the KSHV SGL-1 genomic clone.
FIG. 2 shows the alignment of the general structure of the homologous HVS fragment to the structure of KSHV shown in FIG. 1.

As used herein, the term "isolated" when used in conjunction with a nucleic acid molecule refers to: 1) a nucleic acid molecule which has been separated from an organism or cell in a substantially purified form (i.e. substantially free of other substances originating from that organism or cell), or 2) a nucleic acid molecule having the same nucleotide sequence but not necessarily separated from the organism (i.e. synthesized or recombinantly produced nucleic acid molecules).

As further used herein, the terms "corresponding to" or "having" or "as shown in" or "consisting of" when used in conjunction with a SEQ ID NO for a nucleotide sequence refer to a nucleotide sequence which is substantially the same nucleotide sequence, or derivatives thereof (such as deletion and hybrid variants thereof, splice variants thereof, etc.). Nucleotide additions, deletions, and/or substitutions, such as those which do not affect the translation of the DNA molecule, are within the scope of a nucleotide sequence corresponding to or having or as shown in or consisting of a particular nucleotide sequence (i.e. the amino acid sequence encoded thereby remains the same). Such additions, deletions, and/or substitutions can be, for example, the result of point mutations made according to methods known to those skilled in the art. It is also possible to substitute a nucleotide which alters the amino acid sequence encoded thereby, where the amino acid substituted is a conservative substitution or where amino acid homology is conserved. It is also possible to have minor nucleotide additions, deletions, and/or substitutions which do not alter the function of the resulting protein. These are also within the scope of a nucleotide sequence corresponding to or having or as shown in or consisting of a particular nucleotide sequence.

Similarly, the term "corresponding to" or "having" or "as shown in" or "consisting of" when used in conjunction with a SEQ ID NO for an amino acid sequence refers to an amino acid sequence which is substantially the same amino acid sequence or derivatives thereof. Amino acid additions, deletions, and/or substitutions which do not negate the ability of the resulting protein to form a functional protein are within the scope of an amino acid sequence corresponding to or having or as shown in or consisting of a particular amino acid sequence. Such additions, deletions, and/or substitutions can be, for example, the result of point mutations in the DNA encoding the amino acid sequence, such point mutations made according to methods known to those skilled in the art. Substitutions may be conservative substitutions of amino acids. Two amino acid residues are conservative substitutions of one another, for example, where the two residues are of the same type. In this regard, alanine, valine, leucine, isoleucine, glycine, cysteine, phenylalanine, tryptophan, methionine, and proline, all of which are non-polar residues, are of the same type. Serine, threonine, tyrosine, asparagine, and glutamine, all of which are uncharged polar residues, are of the same type. Another type of residue is the positively charged (basic) polar amino acid residue, which includes histidine, lysine, and arginine. Aspartic acid and glutamic acid, both of which are negatively charged (acidic) polar amino acid residues, form yet another type of residue. Further descriptions of the concept of conservative substitutions are given by French and Robson 1983, Taylor 1986, and Bordo and Argos 1991.

As further used herein, the term "corresponding to" or "having" or "as shown in" or "consisting of" when used in conjunction with a SEQ ID NO for a nucleotide or amino acid sequence is intended to cover linear or cyclic versions of the recited sequence (cyclic referring to entirely cyclic versions or versions in which only a portion of the molecule is cyclic, including, for example, a single amino acid cyclic upon itself), and is intended to cover derivative or modified nucleotide or amino acids within the recited sequence. For example, those skilled in the art will readily understand that an adenine nucleotide could be replaced with a methyladenine, or a cytosine nucleotide could be replaced with a methylcytosine, if a methyl side chain is desirable. Nucleotide sequences having a given SEQ ID NO are intended to encompass nucleotide sequences containing these and like derivative or modified nucleotides, as well as cyclic variations. As a further example, those skilled in the art will readily understand that an asparagine residue could be replaced with an ethylasparagine if an ethyl side chain is desired, a lysine residue could be replaced with a hydroxylysine if an OH side chain is desired, or a valine residue could be replaced with a methylvaline if a methyl side chain is desired. Amino acid sequences having a given SEQ ID NO are intended to encompass amino acid sequences containing these and like derivative or modified amino acids, as well as cyclic variations. Cyclic, as used herein, also refers to cyclic versions of the derivative or modified nucleotides and amino acids.

With these definitions in mind, the subject invention provides an isolated nucleic acid molecule encoding a protein of Kaposi's sarcoma associated herpesvirus (KSHV). The nucleic acid molecule can be deoxyribonucleic acid (DNA) or ribonucleic acid (RNA), the latter including messenger RNA (mRNA). The nucleic acid can be genomic or recombinant, biologically isolated or synthetic.

The DNA molecule can be a cDNA molecule, which is a DNA copy of an mRNA encoding the protein.

In one embodiment, the protein of KSHV is an antigenic membrane protein. This antigenic membrane protein is encoded by the nucleotide sequence as shown in SEQ ID NO:14 and has an amino acid sequence as shown in SEQ ID NO:15.

In a further embodiment, the protein of KSHV is a G protein coupled receptor. This receptor protein is encoded by the nucleotide sequence as shown in SEQ ID NO:16 and has an amino acid sequence as shown in SEQ ID NO:17.

In a still further embodiment, the protein of KSHV is a cyclin protein, preferably a cyclin D protein. This cyclin protein is encoded by the nucleotide sequence as shown in SEQ ID NO:18 and has an amino acid sequence as shown in SEQ ID NO:19.

The invention also provides an antisense nucleic acid molecule that is complementary to the mRNA encoding the protein, or a fragment thereof. Antisense nucleic acid molecules can be RNA or single-stranded DNA, and can be complementary to the entire mRNA molecule encoding the protein (i.e. of the same nucleotide length as the entire molecule). It may be desirable, however, to work with a shorter molecule which is a fragment thereof. These shorter antisense molecules are capable of hybridizing to the mRNA encoding the entire molecule, and preferably consist of at least twenty nucleotides. These antisense molecules can be used to reduce levels of the protein, by introducing into cells an RNA or single-stranded DNA molecule that is complementary to the mRNA of the protein (i.e. by introducing an antisense molecule). The antisense molecule can base-pair with the mRNA of the protein, preventing translation of the mRNA into protein. Thus, an antisense molecule to the protein can prevent translation of mRNA encoding the protein into a functional protein.

More particularly, an antisense molecule complementary to mRNA encoding a protein of KSHV can be used to decrease expression of a functional protein of KSHV. A cell with a first level of expression of a functional protein of KSHV is selected, and then the antisense molecule is introduced into the cell. The antisense molecule blocks expression of functional protein, resulting in a second level of expression of a functional protein in the cell. The second level is less than the initial first level.

Antisense molecules can be introduced into cells by any suitable means. In one embodiment, the antisense RNA molecule is injected directly into the cellular cytoplasm, where the RNA interferes with translation. A vector may also be used for introduction of the antisense molecule into a cell. Such vectors include various plasmid and viral vectors. For a general discussion of antisense molecules and their use, see Han et al. 1991 and Rossi 1995. Suitable cells for introduction of antisense molecules include lymph node cells, peripheral blood B cells, B cell lymphoma cells, endothelial cells, fibroblasts, spindle cells, and macrophages, and particularly include those cells where KSHV is typically found as an infection.

The invention further provides a special category of antisense RNA molecules, known as ribozymes, having recognition sequences complementary to the mRNA encoding the protein, or complementary to a fragment of the mRNA. Ribozymes not only complex with target sequences via complementary antisense sequences but also catalyze the hydrolysis, or cleavage, of the template mRNA molecule. Examples, which are not intended to be limiting, of suitable regions of the mRNA template to be targeted by ribozymes are any regions unique to the particular protein of KSHV such that only the mRNA encoding the particular protein is cleaved. Such unique regions can be identified by comparison of nucleotide sequences.

Expression of a ribozyme in a cell can inhibit gene expression (such as the expression of a protein of KSHV). More particularly, a ribozyme having a recognition sequence complementary to an mRNA encoding a protein of KSHV, or complementary to a fragment of the mRNA, can be used to decrease expression of the protein. A cell with a first level of expression of the protein is selected, and then the ribozyme is introduced into the cell. The ribozyme in the cell decreases expression of the protein in the cell, because mRNA encoding the protein is cleaved and cannot be translated.

Ribozymes can be introduced into cells by any suitable means. In one embodiment, the ribozyme is injected directly into the cellular cytoplasm, where the ribozyme cleaves the mRNA and thereby interferes with translation. A vector may be used for introduction of the ribozyme into a cell. Such vectors include various plasmid and viral vectors. As the skilled practitioner will note, the DNA encoding the ribozyme does not need to be "incorporated" into the genome of the host cell; it could be expressed in a host cell infected by a viral vector, with the vector expressing the ribozyme, for instance. For a general discussion of ribozymes and their use, see Sarver et al. 1990, Chrisey et al. 1991, Rossi et al. 1992, and Christoffersen et al. 1995. Suitable cells for introduction of ribozymes according to the subject invention include lymph node cells, peripheral blood B cells, B cell lymphoma cells, endothelial cells, fibroblasts, spindle cells, and macrophages, particularly those cells where KSHV is typically found as an infection.

The nucleic acid molecules of the subject invention can be expressed in suitable host cells using conventional techniques. Any suitable host and/or vector system can be used to express the KSHV proteins. For in vitro expression, bacterial hosts (for example, *Escherichia coli*) and mammalian hosts (for example, Hela cells, Cv-1 cells, COS cells) are preferred. Expression of the KSHV proteins may be desirable to obtain amounts of the protein for study and/or research purposes, as well as for therapy for virus infections.

Techniques for introducing the nucleic acid molecules into the host cells may involve the use of expression vectors which comprise the nucleic acid molecules. These expression vectors (such as plasmids and viruses; viruses including bacteriophage) can then be used to introduce the nucleic acid molecules into suitable host cells. For example, DNA encoding the protein of KSHV can be injected into the nucleus of a host cell or transformed into the host cell using a suitable vector, or mRNA encoding the protein can be injected directly into the host cell, in order to obtain expression of protein in the host cell.

Various methods are known in the art for introducing nucleic acid molecules into host cells. One method is microinjection, in which DNA is injected directly into the nucleus of cells through fine glass needles (or RNA is injected directly into the cytoplasm of cells). Alternatively, DNA can be incubated with an inert carbohydrate polymer (e.g. dextran) to which a positively charged chemical group (e.g. diethylaminoethyl ("DEAE")) has been coupled. The DNA sticks to the DEAE-dextran via its negatively charged phosphate groups. These large DNA-containing particles, in turn, stick to the surfaces of cells, which are thought to take them in by a process known as endocytosis. Some of the DNA evades destruction in the cytoplasm of the cell and escapes to the nucleus, where it can be transcribed into RNA like any other gene in the cell. In another method, cells efficiently take in DNA in the form of a precipitate with calcium phosphate. In electroporation, cells are placed in a solution containing DNA and subjected to a brief electrical pulse that causes holes to open transiently in their membranes. DNA enters through the holes directly into the cytoplasm, bypassing the endocytotic vesicles through which they pass in the DEAE-dextran and calcium phosphate procedures (passage through these vesicles may sometimes destroy or damage DNA). DNA can also be incorporated into artificial lipid vesicles, liposomes, which fuse with the cell membrane, delivering their contents directly into the cytoplasm. In an even more direct approach, used primarily with plant cells and tissues, DNA is absorbed to the surface of tungsten microprojectiles and fired into cells with a device resembling a shotgun.

Several of these methods, microinjection, electroporation, and liposome fusion, have been adapted to introduce proteins into cells. For review, see Mannino and Gould-Fogerite 1988, Shigekawa and Dower 1988, Capecchi 1980, and Klein et al. 1987.

Further methods for introducing nucleic acid molecules into cells involve the use of viral vectors. Since viral growth depends on the ability to get the viral genome into cells, viruses have devised clever and efficient methods for doing it. One such virus widely used for protein production is an insect virus, baculovirus. Baculovirus attracted the attention of researchers because during infection, it produces one of its structural proteins (the coat protein) to spectacular levels. If a foreign gene were to be substituted for this viral gene, it too ought to be produced at high level. Baculovirus, like vaccinia, is very large, and therefore foreign genes must be placed in the viral genome by recombination. To express a foreign gene in baculovirus, the gene of interest is cloned in place of the viral coat protein gene in a plasmid carrying a small portion of the viral genome. The recombinant plasmid is cotransfected into insect cells with wild-type baculovirus DNA. At a low frequency, the plasmid and viral DNAs recombine through homologous sequences, resulting in the insertion of the foreign gene into the viral genome. Virus plaques develop, and the plaques containing recombinant virus look different because they lack the coat protein. The plaques with recombinant virus are picked and expanded. This virus stock is then used to infect a fresh culture of insect cells, resulting in high expression of the foreign protein. For a review of baculovirus vectors, see Miller 1989. Various viral vectors have also been used to transform mammalian cells, such as vaccinia virus, adenovirus, and retrovirus.

As indicated, some of these methods of transforming a cell require the use of an intermediate plasmid vector. U.S. Pat. No. 4,237,224 to Cohen and Boyer describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture. The DNA sequences are cloned into the plasmid vector using standard cloning procedures known in the art, as described by Sambrook et al. (1989).

Host cells into which the nucleic acid encoding the protein of KSHV has been introduced can be used to produce (i.e. to functionally express) the protein.

Various modifications of the nucleic acid and amino acid sequences disclosed herein are covered by the subject invention. These varied sequences still encode a functional protein of KSHV. The invention thus further provides an isolated nucleic acid molecule encoding a protein of KSHV, the nucleic acid molecule encoding a first amino acid sequence having at least 90% amino acid identity to a second amino acid sequence. The second amino acid sequence is as shown in SEQ ID NO:15 where the protein is an antigenic membrane protein of KSHV; is as shown in SEQ ID NO:17 where the protein is a G protein coupled receptor of KSHV; and is as shown in SEQ ID NO:19 where the protein is a cyclin protein of KSHV.

The invention further provides an isolated DNA oligomer capable of hybridizing to the nucleic acid molecule encoding the protein of KSHV according to the subject invention. Such oligomers can be used as probes in a method of detecting the presence of nucleic acid molecules encoding the KSHV protein in a sample. More particularly, a sample can be contacted with the DNA oligomer, and the DNA oligomer will hybridize to any nucleic acid encoding the KSHV protein present in the sample, forming a complex therewith. The complex can then be detected, thereby detecting presence of nucleic acid molecules encoding the KSHV protein in the sample.

The complex can be detected using methods known in the art. Preferably, the DNA oligomer is labeled with a detectable marker so that detection of the marker after the DNA oligomer hybridizes to nucleic acid sequences for the KSHV protein or closely related proteins in the sample (wherein non-hybridized DNA oligomer has been washed away) is detection of the complex. Detection of the complex indicates the presence of the KSHV protein in the sample. As will be readily apparent to those skilled in the art, such a method could also be used quantitatively to assess the amount of KSHV protein in a sample.

For detection, the oligomers can be labeled with, for example, a radioactive isotope, biotin, an element opaque to X-rays, or a paramagnetic ion. Radioactive isotopes are commonly used and are well known to those skilled in the art. Representative examples include phosphorous-32, sulfur-35, indium-111, technetium-99m, and iodine-123. Biotin is a standard label which would allow detection of the biotin labeled oligomer with avidin. Paramagnetic ions are also commonly used and include, for example, chelated metal ions of chromium (III), manganese (II), and iron (III). When using such labels, the labeled DNA oligomer can be imaged using methods known to those skilled in the art. Such imaging methods include, but are not limited to, autoradiography, fluorography, X-ray, CAT scan, PET scan, NMRI, and fluoroscopy. Other suitable labels include enzymatic labels (horseradish peroxidase, alkaline phosphatase, etc.) and fluorescent labels (such as FITC, rhodamine, etc.).

As should be readily apparent to those skilled in the art, the DNA oligomers must selectively hybridize to nucleic acid molecules encoding the KSHV protein in order to be useful as detecting agents. Therefore, the oligomers must either be of sufficient length to selectively hybridize to nucleic acid molecules encoding KSHV proteins, or the oligomers can be shorter molecules directed to consecutive nucleotides unique to the nucleic acid molecules encoding the KSHV proteins. In either situation, the oligomers will selectively hybridize and detection assays will be accurate. Probes and primers as discussed above also need to have such selectivity to be most useful.

The invention further provides an isolated protein of Kaposi's sarcoma associated herpesvirus. In one embodiment, the protein is an antigenic membrane protein such as the antigenic membrane protein encoded by the amino acid sequence as shown in SEQ ID NO:15. In another embodiment, the KSHV protein is a G protein coupled receptor such as the G protein coupled receptor encoded by the amino acid sequence as shown in SEQ ID NO:17. In a further embodiment, the KSHV protein is a cyclin protein such as the cyclin D protein encoded by the amino acid sequence as shown in SEQ ID NO:19.

A variety of methodologies known in the art can be utilized to obtain an isolated protein of KSHV according to the subject invention. In one method, the protein is purified from KSHV viral particles or from cells infected with KSHV. A suitable source of KSHV is a KSHV cell line, such as the cell line designated BC-2 or BC-3. Each of cell lines BC-2 and BC-3 have been deposited with the American Type Culture Collection (ATCC), 12301 Parklawn Drive, Rockville, Md. 20852, pursuant to and in satisfaction of the requirements of the Budapest Treaty on the International Recognition of the Deposit of Microorganisms for the Purposes of Patent Procedure. BC-2 was deposited as ATCC Accession No. CRL 2231 and BC-3 was deposited as ATCC Accession No. CRL 2277. One skilled in the art can readily isolate the identified KSHV proteins free of natural contaminants using methods such as, for example, immunochromatography, HPLC, size-exclusion chromatography, ion-exchange chromatography, and immunoaffinity chromatography. Alternatively, an isolated KSHV protein according to the subject invention can be purified from cells which have been altered to express the proteins. As used herein, a cell is said to be "altered to express the protein" when the cell, through genetic manipulation, is made to produce the KSHV protein which it normally does not produce or which the cell normally produces at low levels. One skilled in the art can readily adapt procedures for introducing and expressing either genomic, cDNA or synthetic sequences into either eukaryotic or prokaryotic cells in order to generate a cell which produces a KSHV protein utilizing the sequences disclosed herein.

An isolated antigenic membrane protein as defined herein includes antigenic membrane proteins encoded by a first amino acid sequence having at least 90% amino acid identity to a second amino acid sequence, the second amino acid sequence being as shown in SEQ ID NO:15. An isolated G protein coupled receptor as defined herein includes G protein coupled receptors encoded by a first amino acid sequence having at least 90% amino acid identity to a second amino acid sequence, the second amino acid sequence being as shown in SEQ ID NO:17. An isolated cyclin protein as defined herein includes cyclin proteins encoded by a first amino acid sequence having at least 90% amino acid identity to a second amino acid sequence, the second amino acid sequence being as shown in SEQ ID NO:19.

Antibodies can be raised to the KSHV proteins disclosed herein. The invention thus further provides an antibody or fragment thereof specific for the KSHV protein of the subject invention. Antibodies of the subject invention include polyclonal antibodies and monoclonal antibodies capable of binding to the KSHV protein, as well as fragments of these antibodies, and humanized forms. Humanized forms of the antibodies of the subject invention may be generated using one of the procedures known in the art such as chimerization. Fragments of the antibodies of the present invention include, but are not limited to, the Fab, the F(ab')$_2$, and the Fc fragments.

The invention also provides hybridomas which are capable of producing the above-described antibodies. A hybridoma is an immortalized cell line which is capable of secreting a specific monoclonal antibody.

In general, techniques for preparing polyclonal and monoclonal antibodies as well as hybridomas capable of producing the desired antibody are well known in the art (see Campbell 1984 and St. Groth et al. 1980). Any animal (mouse, rabbit, etc.) which is known to produce antibodies can be immunized with the antigenic KSHV protein (or an antigenic fragment thereof). Methods for immunization are well known in the art. Such methods include subcutaneous or intraperitoneal injection of the protein. One skilled in the art will recognize that the amount of the protein used for immunization will vary based on the animal which is immunized, the antigenicity of the protein, and the site of injection.

The protein which is used as an immunogen may be modified or administered in an adjuvant in order to increase the protein's antigenicity. Methods of increasing the antigenicity of a protein are well known in the art and include, but are not limited to, coupling the antigen with a heterologous protein (such as a globulin or beta-galactosidase) or including an adjuvant during immunization.

For monoclonal antibodies, spleen cells from the immunized animals are removed, fused with myeloma cells, such as SP2/O-Ag 15 myeloma cells, and allowed to become monoclonal antibody producing hybridoma cells.

Any one of a number of methods well known in the art can be used to identify the hybridoma cell which produces an antibody with the desired characteristics. These include screening the hybridomas with an ELISA assay, western blot analysis, or radioimmunoassay (Lutz et al. 1988).

Hybridomas secreting the desired antibodies are cloned and the class and subclass are determined using procedures known in the art (Campbell 1984).

For polyclonal antibodies, antibody containing antisera is isolated from the immunized animal and is screened for the presence of antibodies with the desired specificity using one of the above-described procedures.

The present invention further provides the above-described antibodies in detectably labeled form. Antibodies can be detectably labeled through the use of radioisotopes, affinity labels (such as biotin, avidin, etc.), enzymatic labels (such as horseradish peroxidase, alkaline phosphatase, etc.), fluorescent labels (such as FITC, rhodamine, etc.), paramagnetic atoms, and the like. Procedures for accomplishing such labeling are well known in the art, such as the procedures described in, for example, Sternberger et al. 1970, Bayer et al. 1979, Engval et al. 1972, and Goding 1976.

The labeled antibodies or fragments thereof of the present invention can be used for in vitro, in vivo, and in situ assays to identify cells or tissues which express KSHV proteins, to identify samples containing KSHV proteins, or to detect the presence of KSHV proteins in a sample. More particularly, the antibodies or fragments thereof can thus be used to detect the presence of KSHV protein in a sample, by contacting the sample with the antibody or fragment thereof. The antibody or fragment thereof binds to the KSHV protein if present in the sample, forming a complex therewith. The complex can then be detected, thereby detecting the presence of the KSHV protein in the sample. As will be readily apparent to those skilled in the art, such a method could also be used quantitatively to assess the amount of a KSHV protein in a sample.

Fragments of the nucleic acid molecules encoding the KSHV proteins are also provided, and are best defined in the context of amino acid sequence relationships among members of the protein sequence family and information on the function of these proteins and specific protein domains. For example, G protein coupled receptors are known to have seven membrane spanning domains. The portion of the nucleic acid molecule encoding a domain could be a useful fragment. As a further example, the portion of the nucleic acid molecule encoding the cyclin box motif of the cyclin D protein of KSHV could be a useful fragment. Antibodies prepared to a polypeptide encoded by conserved determinants of a KSHV protein would therefore be expected to be of use as reagents capable of detecting many members of the protein family (i.e., members of G protein coupled receptor families, or cyclin D families). Such antibodies, if introduced into cells that express a member of the protein family, would also be expected to modify the normal function of the particular type of protein expressed in those cells. In contrast, antibodies can be prepared which are directed to an amino acid sequence that is less well conserved within the protein family. Antibodies prepared to the polypeptide encoded by this less well conserved fragment would therefore be expected to recognize selectively the KSHV protein from which the fragment was derived.

The present invention also provides a method for detecting infection of a cell by Kaposi's sarcoma associated herpesvirus. The method includes detecting presence of a protein of KSHV in the cell. For example, the cell can be disrupted to expose the cellular proteins, and the disrupted cell can be contacted with an antibody or fragment thereof, preferably labeled with a detectable marker, specific for a KSHV protein according to the subject invention. The antibody or fragment thereof binds to any of the KSHV protein present in the disrupted cell, forming a complex therewith. By detecting the complex, the presence of a KSHV protein in the sample is detected. Alternatively, the presence of a KSHV protein in the cell can be detected by disrupting the cell to expose the cellular DNA, contacting the disrupted cell with a DNA oligomer, preferably labeled with a detectable marker, capable of hybridizing to a nucleic acid molecule encoding a KSHV protein. The DNA oligomer hybridizes to any nucleic acid encoding the KSHV protein present in the disrupted cell, forming a complex therewith. Detection of the complex indicates the presence of a nucleic acid molecule encoding a KSHV protein.

Leader sequences can be employed for targeting of the nucleic acid molecule or protein of the subject invention to the desired cell or part of a cell. It should be readily apparent to those skilled in the art that a Met residue may need to be added to the amino terminal of the amino acid sequence of a mature KSHV protein (e.g. to SEQ ID NO:15, 17, or 19) or an ATG added to the 5' end of a nucleotide sequence (e.g. to SEQ ID NO:14, 16, or 18), in order to express the protein in some host cells. The Met version of the mature KSHV protein is thus specifically intended to be covered by reference to SEQ ID NOs. After expression of a leader/KSHV protein construct, the leader targets the KSHV protein within a cell before the leader peptide is cleaved from the mature KSHV protein. Any reference to nucleic acid molecules and/or proteins herein is intended to cover such nucleic acid molecules and/or proteins if such leader sequences are added thereto.

The present invention is further illustrated by the following examples.

MATERIALS AND METHODS

Genomic library and cloning. Genomic DNA was obtained from a pathologic specimen of a primary effusion lymphoma, corresponding to Case 1 previously described (Cesarman et al. 1995a). The DNA was digested to completion with Bgl II restriction endonuclease (Boehringer-Mannheim, Indianapolis, Ind.), and the DNA fragments between 9 and 23 kb of length were isolated by agarose gel electrophoresis fractionation. These fragments were cloned into the LambdaGEM-11 vector as per the manufacturer's instructions (Promega, Madison, Wis.). The SGL-1 clone was identified by hybridization to the KS631 Bam probe (Chang et al. 1994), and subsequently purified using standard plating methods (Maniatis et al. 1982).

Genomic sequencing. The SGL-1 bacteriophage clone was digested with BamHI, and the 8 fragments obtained were isolated by gel electrophoresis and subcloned into the pGem3Z vector (Promega, Madison, Wis.). Similarly, this clone was digested with SacI, and the two larger fragments were subcloned in pGem3Z (see FIG. 1 for BamHI and SacI restriction maps). Sequencing was performed using the Taq DyeDeoxy terminator cycle sequencing system with an ABI 373A automated DNA sequencer (Applied Biosystems Inc., Foster City, Calif.). Both strands were sequenced by primer walking and nested deletions. The regions containing open reading frames 75, 74 and 72 (ORF 75, ORF 74 and ORF 72, respectively) were completely sequenced with an average 5 fold redundancy.

Nucleotide composition of the SGL-1 clone. The sequence of this portion of the KSHV genome has an overall G+C content of 54% and an A+T content of 46%. This is similar to the overall G+C content of EBV (60%) and equine herpesvirus 2 (57%), another gamma-2 herpesvirus (Telford et al. 1995). In contrast, HVS has a high G+C content only in its terminal repeats (H-DNA), and a low G+C content in its coding regions (L-DNA, 35% G+C) (Honess et al. 1989). The observed/expected CpG dinucleotide ratio is 0.57. A low overall percentage of CpG dinucleotides is a feature common to gamma herpesviruses, and is thought to result from 5-methylcytosine deamination of methylated CpG residues. This process may be related to the ability of gamma-herpesviruses to maintain a latent state in actively dividing cells (Honess et al. 1989). The low CpG content identified in this region of KSHV is in contrast to the 0.92 observed:expected CpG ratio for the region extending from KSHV ORF 26 through ORF 35 (Moore et al. 1996a). This discrepancy is probably due to regional variation in CpG methylation, since some privileged sites in EBV and HVS seem to be protected from methylation (Honess et al. 1989). The ORF 20–35 region has been resequenced from a PEL cell line library and shows minimal variation from a clone derived from a KS genomic library. Thus, it is unlikely that strain variation accounts for variation in CpG content between these two regions.

Homology, open reading frame (ORF) and translation analysis: Analysis of the DNA sequences for the presence of ORFs, and for their translation products was performed with the Mac Vector 4.1.4 program (Eastman Kodak-IBI, New Haven, Conn.). The BLASTX program was used to search the KSHV DNA sequences for homologous protein sequences (Altschul et al. 1990). Protein sequence databases searched using this program include NBRF PIR, SWISS-PROT, GenPept (translated coding sequences from GenBank) and PDB (Brookhaven Protein Data Bank). The sequences were aligned to homologous genes with the ALIGN program from EERIE (Ecole pour les Etudes et la Recherche en Informatique et Electronique, France).

EXAMPLE I

Three ORFs were identified in the SGL-1 clone and designated ORF75, 74 and 72 according to their location and homology to the HVS genome (FIG. 1 and FIG. 2) (Albrecht et al. 1992), consistent with the orientation and nomenclature adopted for KSHV by Moore et al. (Moore et al. 1996a). A map showing the relative locations of these three ORFs is shown in FIG. 1. MA stands for membrane antigen, GCR is the G protein-coupled receptor homolog and CYC is the cyclin homolog. The restriction map for BamHI (B) and for SacI (S) is shown, and the region containing multiple internal repeats is depicted by the checkered box. The sequences of the ORFs having homology to known genes have been submitted to GenBank under the following Accession numbers: U24269 (ORF75; membrane antigen homolog); U24275 (ORF74; G-protein coupled receptor homolog); and U24276 (ORF72; cyclin homolog).

All three ORFs are colinear and homologous with similar genes in HVS and are present in the same transcriptional orientation. Only one of these genes, ORF75, shows homology to EBV. ORFs 75, 74 and 72 have other viral and/or cellular counterparts as illustrated in Table I and as follows:

ORF75: This ORF (SEQ ID NO:14) is located between nucleotides 83 and 4012 of the SGL-1 clone, encoding a putative protein of 1310 amino acids (SEQ ID NO:15). The translated product of this sequence shows significant homology to ORF75 of HVS, a 152/160K membrane antigen (Cameron et al. 1987), as well as the corresponding gene products in equine herpesvirus 2 (Telford et al. 1995) and the alcelaphine herpesvirus 1 (Ensser and Fleckenstein 1995). It also shows more limited homology to the EBV BNRF1 ORF, encoding the membrane antigen p140 (Baer et al. 1984). These are thought to be nonglycosylated, or poorly glycosylated, structural components of the tegument layer surrounding the capsid. However, the translated product of ORF75 also has full length homology to the purine biosynthetic enzyme phosphoribosylformylglycinamidine synthase (or formylglycineamide ribotide amidotransferase, FGARAT) from *Drosophila melanogaster, Ceanorhabditis elegans* and *Escherichia coli* (Sampei and Mizobuchi 1989; Tiong and Nash 1993; Wilson et al. 1994), suggesting that the protein encoded by this open reading frame may also have a biosynthetic function.

ORF74: This ORF (SEQ ID NO:16) is located between nucleotides 4129 and 5154 of the SGL-1 clone, and encodes a putative protein of 342 amino acids (SEQ ID NO:17). It is transcribed in the opposite direction with respect to the other ORFs in this clone. The putative translation product of this ORF shows homology to the ORF74 of HVS which encodes a G protein-coupled receptor (GCR) homolog (ECRF3) (Nicholas et al. 1992). It also shows homology to multiple mammalian GCRs, of which the highest is to the interleukin 8 receptors, but also includes the GCR involved in HIV cell fusion and entry, and to a lesser degree the type I angiotensin II receptor and the bradykinin receptor (Table 1) (Federsppiel et al. 1993; Feng et al. 1996; Herzog et al. 1993; Jazin et al. 1993; Murphy and Tiffany 1991; Nomura et al. 1993). There is no counterpart of this gene in the EBV genome, although EBV induces the expression of cellular G protein-coupled receptors (Birkenbach et al. 1993; Dobner et al. 1992), which are also homologous to the putative product of KSHV ORF74. As expected for a G protein-coupled receptor, the translated product of ORF74 contains seven hydrophobic regions, theoretically corresponding to transmembrane domains, as predicted by the TMpred program from ISREC (Swiss Institute for Experimental Cancer Research, Switzerland) (Hofmann and Stoffel 1993). The KSHV G protein-coupled receptor homolog also shares other features with members of this class of receptors, including glycosylation sites in the most N-terminal extracellular fragment, and two cysteine residues, in the putative second and third extracellular loops, which are conserved among all G protein-coupled receptors (Strader et al. 1994).

ORF72: This ORF (SEQ ID NO:18) is located between 569 and 1343 bp upstream from the 3' end of the SGL-1 clone and encodes a putative protein of 257 amino acids (SEQ ID NO:19). This ORF shows homology to ORF72 of HVS which encodes a cyclin D homolog (ECLF2) (Nicholas et al. 1992). It also shows homology to multiple mammalian cyclin D proteins, as well as more limited homology to other cyclins (Table 1). Within this ORF, nucleotides 142 to 603 of SEQ ID NO:18 bracket a region with homology to the cyclin box motif (Chang et al. 1996).

Expression analysis of KSHV in KS and PEL. Expression of the three ORFs identified was evaluated by reverse-transcription polymerase chain reactions (RT-PCR) using RNA obtained from two tissues with KS and the two PEL cell lines (BC-1 and BC-2) previously described (Cesarman et al. 1995b). Total RNA was isolated using the TRI REAGENT nucleic acid extraction method (Molecular Research Center Inc., Cincinnati, Ohio) according to the manufacturer's instructions. In order to eliminate any contaminating genomic DNA, the RNA samples were first treated with 2 U RNase-free DNaseI (Boehringer Mannheim, Indianapolis, Ind.) according to the manufacturer's instructions, with subsequent heat-inactivation of the enzyme. The reverse transcription reaction was carried out on 1 µg RNA with 0.5 ng random hexamers and the SUPERSCRIPT™ reverse transcriptase system (GIBCO-BRL, Gaithersburg, Md.) according to the manufacturer's instructions.

The sequences of the primers and the probes used to detect transcripts from the three long ORFs identified are as follows: ORF75:P2 (5' primer), SEQ ID NO:1: 5'-AGGAGCGAGAGAGACGGGAT-3', P7 (3' primer), SEQ ID NO:2: 5'-CCAGGTGCCTGCCCACTTCC-3' and ORF75 probe, SEQ ID NO:3: 5'-CCTAGCTCTTGCAGCAGAAC-3'; ORG74: P8 (5' primer), SEQ ID NO:4: 5'-CGGGGTGCCTTACACGTGG-3', P9 (3' primer), SEQ ID NO:5: 5'-CAGTCTGCAGTCATGTTTCC-3' and ORF74 probe, SEQ ID NO:6: 5'-TGTGTGCGTCAGTCTAGTGAG-3'; ORF72: P51 (5' primer), SEQ ID NO:10: 5'-CACCCTGAAACTCCAGGC-3', P32 (3' primer), SEQ ID NO:11: 5'-GATCCGATCCTCACATAGCG-3' and ORF72 probe, SEQ ID NO:12: 5'-CGCCACTCTATATGCAAACTG-3'. A fourth set of primers/probe were used in connection with a further open reading frame, ORF73, as follows: ORF73: P47 (5' primer), SEQ ID NO:7: 5'-GCAGTCTCCAGAGTCTTCTC-3', P16 (3' primer), SEQ ID NO:8: 5'-CGGAGCTAAAGAGTCTGGTG-3' and ORF73 probe, SEQ ID NO:9: 5'-TGGAGGTGTAGTCTGCTGCG-3'. A primer set specific for the human β-actin cDNA (STRATAGENE, LaJolla, Calif.) was used as a quantitative control. The sequence of the β-actin internal oligonucleotide probe is: SEQ ID NO:13: 5'-GGATGTCCACGTCACACTTC-3'.

The first strand cDNA samples were subjected to direct PCR using 10 pmol of each 5' and 3' primer, in the presence of 1.5 mM MgCl$_2$, and 200 µM dNTPs (KSHV reactions) or 100 µM dNTPs (β-actin reactions). Reactions were performed in a DNA thermal cycler (Perkin-Elmer Cetus, Norwalk, Conn.) and were subjected to an initial 1.5 minutes denaturation at 94° C., followed by 30 cycles of denaturation (1 minute at 94° C.), annealing (2 minutes at 55° C.), and extension (3 minutes at 72° C.). The same reactions were also performed using RNA in the absence of the reverse transcription reaction as a control to exclude the presence of genomic DNA as the source of template for the amplified products. Following agarose gel electrophoresis, amplified products were transferred to a nitrocellulose membrane according to Southern (Southern 1975). Filters were hybridized with a $^{32}$P end-labeled internal oligonucleotide probe as previously described (Frank et al. 1995) and washed for 15 minutes at room temperature, followed by 10 minutes at 57° C. (ORF74 and β-actin), 55° C. (ORF72), or 54° C. (ORF75). The filters were exposed to film at –80° C. with an intensifying screen for 45 minutes to 2 hours, and for 48 hours for the experiments without a reverse transcription step.

Transcripts from all three ORFs were identified in KS and the two PEL cell lines, BC-1 and BC-2. The specificity of this amplification was confirmed by hybridization to a radiolabeled internal oligonucleotide. The observed bands were a result of RNA amplification, and not contamination by genomic DNA, since PCR products were not identified when using the DNAse-treated preparations in the absence of the reverse transcription reaction, even after hybridization with an internal oligonucleotide probe and longer autoradiographic exposures. For the most part, the KSHV transcripts appeared to be more abundant in the PELs than in KS, which is consistent with the higher genomic copy number in the former (Cesarman et al. 1995a), although this is a rough estimate, since quantitative PCR was not performed. All specimens, including the KSHV-negative control, have comparable amounts of RNA as seen using the β-actin set of primers and probe. Expression of all three open reading frames was confirmed in the BC-1 and/or BC-2 cell lines by Northern blot hybridization, excluding the possibility of RT-PCR artifacts.

EXAMPLE II

Implications of the presence and expression of KSHV GCR and cyclin homologs. Three complete ORFs were identified within the KSHV fragment sequenced in this study. only one of these ORFs is present in the EBV genome, while HVS possesses analogous genes in the same order and orientation to all three KSHV ORFs identified. This suggests that KSHV is more closely related to HVS than to EBV, a finding that is consistent with the formal phylogenetic analysis of conserved amino acid sequences (Moore et al. 1996a). The genomes of EBV and HVS are largely conserved and colinear, with the exception of specific sets of genes, notably including those with important pathophysiologic functions such as lymphoid immortalization and transformation. For example, the EBV LMP and EBNA genes are not found in HVS, and the HVS transforming gene, STP, is not present in the EBV genome. This also may be the case for ORFs 74 and 72 which encode a GCR and a cyclin homolog, respectively. While neither of these are present in the EBV genome, expression of cellular members of both the GCR and cyclin D families is induced by EBV encoded proteins (Arvanitakis et al. 1995; Birkenbach et al. 1993; Dobner et al. 1992).

G protein-coupled receptors represent a very large and diverse family of molecules, responding to a variety of hormone and neurotransmitter agonists, ranging from small biogenic amines like epinephrine and histamine, to peptides like bradykinin, and large glycoprotein hormones such as luteinizing and parathyroid hormones (Strader et al. 1994). The KSHV GCR homolog has structural features believed to be functionally important for this class of receptors. Many members of this class of receptors are involved in cell growth and differentiation, and specific members of this family have been found to be involved in malignant transformation, including the human mas oncogene which encodes an angiotensin receptor and is tumorigenic in nude mice (Jackson et al. 1988; Young et al. 1986), and several others which have the ability to transform fibroblasts in an agonist-dependent manner (Allen et al. 1991; Gutkind et al. 1991; Julius et al. 1989). Furthermore, activating mutations of the thyroid-stimulating hormone (TSH) receptor have been found in thyroid adenomas and carcinomas (Parma et al. 1993; Russo et al. 1995).

The closest cellular homologs to ORF74, the KSHV GCR, are the interleukin-8 (IL-8) receptor types A and B, and the closest viral homolog to this protein is the HVS ECRF3 gene, which has been shown to encode a functional IL-8 receptor (Ahuja and Murphy 1993). IL-8 belongs to the α chemokine family of molecules, which are structurally related 70 to 90 amino acid polypeptides involved in inflammation. Thus, it is likely that the KSHV GCR may function as a chemokine receptor. A functional characterization of this receptor is important for understanding the role of KSHV in KS, since IL-8 is a potent angiogenic factor and KS cells have been found to express appreciable levels of IL-8 (Sciacca et al. 1994). Furthermore, EBV-immortalized lymphoblastoid cells and some neoplastic B cells have also been found to produce IL-8 (di Celle et al. 1994; di Celle et al. 1996; Merico et al. 1993; Wolf et al. 1995), although little is known regarding the presence of IL-8 receptors on B cells and their response to IL-8. Interestingly, the KSHV GCR is also homologous to another member of this family of receptors, the "fusin" protein, a necessary cofactor for HIV fusion and cell entry which has been recently described (Feng et al. 1996). This receptor had been previously identified by several investigators, but its natural ligand remains unknown (Federsppiel et al. 1993; Herzog et al. 1993; Jazin et al. 1993; Nomura et al. 1993). This finding raises the possibility that the KSHV GCR may also be involved in some viral/cellular interactions.

The putative protein encoded by ORF72 is homologous to the HVS cyclin homolog and to multiple mammalian cyclins, in particular to members of the cyclin D family. Cyclins are required for cellular division, and thus play a key role in cellular proliferation (Peters 1994). Furthermore, one of the human cyclins, cyclin D1, is the PRAD1 oncogene implicated in the development of certain parathyroid tumors (Arnold et al. 1989; Motokura et al. 1991) and hepatocellular carcinomas (Zhang et al. 1993). Cyclin D1 is also the gene involved in the bcl-1 translocation breakpoint present in mantle cell lymphomas (Tsujimoto et al. 1984). The HVS cyclin has been found to be functional, as it associates with cdk6 and is able to activate protein kinase activity (Jung et al. 1994). In vitro functional studies show that KSHV cyclin has kinase activity as demonstrated by the phosphorylation of the retinoblastoma protein leading to its inactivation (Chang et al. 1996).

All three ORFs identified were expressed at the RNA level in the KS and PEL specimens analyzed. The PEL cell cultures studied (BC-1 and BC-2) are composed mainly of latently infected proliferating cells, but have a small proportion of cells which are permissive for virus replication, as documented by the appearance of cytopathic changes in these cells, the ability to transmit the virus, and the presence of viral particles containing KSHV DNA in the culture supernatants (Cesarman et al. 1995b; Mesri et al. 1996; Moore et al. 1996a). Thus, perhaps unlike the BCBL-1 cells reported by Renne et al. (Renne et al. 1996), the BC-1 and BC-2 cells do not appear to be tightly latent, and expression of ORF72, 74 and 75 in these cell lines could be a result of either latent or lytic infection. However, induction experiments using TPA and phosphonoacetic acid demonstrate that at least the cyclin gene is expressed during latent infection in the BC-1 cell line. The finding of expression of these three ORFs in KS appears to contrast with the recent study by Zhong et al. (Zhong et al. 1996), in which expression of only two transcripts was identified by Northern blot analysis using probes spanning 120 Kb of the KSHV genome, and apparently including the region reported herein. While neither of these transcripts corresponds to the ORFs described herein, this discrepancy is explained by the large difference in sensitivity of the Northern blot analysis performed by Zhong et al. and the RT-PCR analysis herein. Furthermore, the amount of KSHV DNA is highly variable from one KS lesion to another (Chang et al. 1994), and thus the amount of KSHV RNA is likely to be likewise variable. Thus, differences in the KS samples analyzed may account for detection of specific transcripts in some but not in other KS specimens.

The presence and expression of KSHV G protein-coupled receptor and cyclin homologs, both of which are genes that control cellular proliferation and/or differentiation, provides strong evidence that KSHV is an oncogenic virus. This finding supports the epidemiologic evidence that KSHV plays an active role in the pathogenesis of Kaposi's sarcoma and primary effusion lymphomas.

TABLE I

Homology of ORF's Identified in Clone SGL-1 to Corresponding Viral and Cellular Genes.

| KSHV | GENE HOMOLOG | % Identity | % Similarity |
|---|---|---|---|
| ORF75 | EHV 2-ORF75 | 34 | 71 |
| | HVS-ORF75 | 34 | 72 |
| | AHV 1-P140 | 20 | 65 |
| | EBV-P140 | 29 | 67 |
| | D. MELANOGASTER-FGARAT | 20 | 66 |
| | C. ELEGANS-FGARAT | 18 | 62 |
| ORF74-GCR | HVS-ORF74 | 32 | 71 |
| | IL8-R-B-HU | 27 | 74 |
| | IL8-R-A-HU | 25 | 70 |
| | BLR1 | 23 | 66 |
| | EHV 2-U20824 | 21 | 66 |
| | LESTR (FUSIN) | 20 | 66 |
| | HCMV-US28 | 20 | 65 |
| ORF72-CYC | HVS-ORF72 | 33 | 74 |
| | CYCLIN D2 | 27 | 64 |
| | CYCLIN D3 | 26 | 67 |
| | CYCLIN D1 | 24 | 61 |
| | CYCLIN A | 14 | 43 |

Abbreviations: EHV 2: equine herpesvirus 2; HVS: herpesvirus saimiri; AHV 1: alcelaphine herpesvirus 1; FGARAT: phosphoribosylformylglycinamidine synthase; IL8-R: interleukin 8 receptor; HCMV: human cytomegalovirus; BLR1: Burkitt's lymphoma receptor 1; LESTR: leukocyte-derived seven transmembrane domain receptor.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

LIST OF REFERENCES CITED

Ahuja, S. K., and P. M. Murphy. 1993. J. Biol. Chem. 268:220691–20694.
Albrecht, J. -C., et al. 1992. J. Virol. 66:5047–5058.
Allen, L. F., et al. 1991. Proc. Natl. Acad. Sci. USA 88:11354–11358.
Altschul, S. F., et al. 1990. J. Mol. Biol. 215:403–410.
Ambroziak, J. A., et al. 1995 Science. 268:582–583.
Arnold, A. K., et al. 1989. J. Clin. Invest. 83:2034–2040.
Arvanitakis, L., et al. 1996. Blood. 88:2648–2654.
Arvanitakis, L., et al. 1995. J Immunol. 155:1047–1056.
Baer, R., et al. 1984. Nature. 310:207–211.
Bayer, E. A., et al. 1979. Meth. Enzym. 62:308.
Biesinger, B., et al. 1992. Proc. Natl. Acad. Sci. USA 89:3116–3119.
Birkenbach, M., et al. 1993. J. Virol. 67:2209–2220.
Bordo, D., and Argos, P. 1991. J. Mol. Biol. 217:721–729.
Boshoff, C., et al. 1995. Lancet. 345:1043–1044.
Cameron, K. R., et al. 1987. J. Virol. 61:2063–2070.
Campbell, A. M.. 1984. *Monoclonal Antibody Technology: Laboratory Techniques in Biochemistry and Molecular Biology.* Elsevier Science Publishers, Amsterdam, The Netherlands.
Capecchi, M. 1980. Cell 22:479–488.
Cesarman, E., et al. 1995a. N. Engl. J. Med. 332:1186–1191.
Cesarman, E., et al. 1995b. Blood. 86:2708–2714.
Chang, Y., et al. 1994. Science. 266:1865–1869.
Chang, Y., et al. 1996. Nature. 382:410.
Chang, Y., et al. 1996. Arch Intern Med. 156:202–204.
Chrisey, L., et al. 1991. Antisense Research and Development 1:57–63.
Christoffersen, R. E., and Marr, J. J. 1995. Journal of Medicinal Chemistry 38:2023–2037.
di Celle, P. F., et al. 1994. Blood. 84:220–228.
di Celle, P. F., et al. 1996. Blood. 87:4382–4389.
Dobner, T., et al. 1992. Eur. J. Immunol. 22:2795–2799.
Dupin, N., et al. 1995a. N. Engl. J. Med. 333:798.
Dupin, N., et al. 1995b. Lancet. 345:761–762.
Engval, E., et al. 1972. Immunol 109:129.
Ensser, A., and B. Fleckenstein. 1995. J. Gen. Virol. 75:1063–1067.
Federsppiel, B., et al. 1993. Genomics. 16:707–12.
Feng, Y., et al. 1996. Science. 272:872–877.
Fleckenstein, B., and R. C. Desrosiers. 1982. p. 253–332. In B. Roizman (ed.), *The herpesviruses.* Plenum Press, New York.
Frank, D., et al. 1995. Blood. 85:1396–1403.
French, S., and Robson, B. 1983. J. Molecular Evolution 19:171–175.
Gessain, A., et al. 1995. Blood. 87:414–416.
Goding, J. W. 1976. J. Immunol. Meth. 13:215.
Gutkind, J. S., et al. 1991. Proc. Natl. Acad. Sci. USA 88:4703–4707.
Han, L., et al. 1991. Proc. Natl. Acad. Sci. USA 88:4313–4317.
Herzog, H., et al. 1993. DNA Cell. Biol. 12:465–71.
Hofmann, K., and W. Stoffel. 1993. Biol. Chem. Hoppe-Seyler. 347:166.
Honess, R. W., et al. 1989. J. Gen. Virol. 70:837–855.
Jackson, T. R., et al. 1988. Nature. 335:437–440.
Jazin, E. E., et al. 1993. Regul. Pept. 47:247–58.
Julius, D., et al. 1989. Science. 244:1057–1062.
Jung, J. U., et al. 1994. Mol. Cell. Biol. 14:7235–7244.
Karcher, D. S., and S. Alkan. 1995. N. Engl. J. Med. 333:797–798.
Klein, T. M., et al. 1987. Nature 327:70–73.
Lutz, et al. 1988. Exp. Cell. Res. 175:109–124.
Maniatis, T., et al. 1982. *Molecular cloning. A laboratory manual.* Cold Spring Harbor Laboratory, Cold Spring Harbor, N.Y.
Mannino, R. J., and Gould-Fogerite, S. 1988. BioTechniques 6:682–690.
Merico, F., et al. 1993. Clin Exp. Immunol. 92:27–31.
Mesri, E. A., et al. 1996. J. Exp. Med. 183:2385–2390.
Miller, L. K. 1989. Bioassays 11:91–95.
Miller, G. 1990. p. 1021–1058. In B. N. Fields et al. (eds.), *Virology,* Second Edition, Raven Press, Ltd., New York.
Moore, P. S., and Y. Chang. 1995. N. Engl. J. Med. 332:1181–1185.
Moore, P. S., et al. 1996a. J. Virol. 70:549–558.
Moore, P. S., et al. 1996b. AIDS. 10:175–180.
Motokura, T., et al. 1991. Nature. 350:512–515.
Murphy, P. M., and H. L. Tiffany. 1991. Science. 253:1280–1283.
Nicholas, J., et al. 1992. Nature. 355:362–5.
Noel, J. C. 1995. The Lancet. 346:1359.
Nomura, H., et al. 1993. Int. Immunol. 5:1239–49.
Parma, J., et al. 1993. Nature. 365:649–651.
Peters, G. 1994. J. Cell Sci. 18:89–96.
Renne, R., et al. 1996. Nat. Med. 2:342–346.
Rossi, J. J., et al. 1992. AIDS Research and Human Retroviruses 8(2):183–189.
Rossi, J. J. 1995. British Medical Bulletin 51(1):217–225.
Russo, D., et al. 1995. Oncogene. 11:1907–1911.
Said, J. W., et al. 1996. Blood. 87:4937–4943.
Sambrook et al. 1989. *Molecular Cloning: A Laboratory Manual,* 2d Edition, Cold Spring Harbor Laboratory Press, Cold Spring Harbor, N.Y.

Sampei, G., and K. Mizobuchi. 1989. J. Biol. Chem. 264:21230–21238.
Sarver, N., et al. 1990. Science. 247:1222–1225.
Schalling, M., et al. 1995. Nat. Med. 1:707–708.
Sciacca, F. L., et al. 1994. J. Immunol. 153:4816–4825.
Shigandia, D., et al. 1995. The Lancet. 346:1359–1360.
Shigekawa, K., and Dower, W. J. 1988. BioTechniques 6:742–751.
Soulier, J., et al. 1995. Blood. 86:1275–1280.
Southern, E. M. 1975. J. Mol. Biol. 98:503–517.
Sternberger, L. A., et al. 1970. J Histochem. Cytochem. 18:315.
St. Groth, et al. 1980. J. Immunol. Methods 35:1–21.
Strader, C. D., et al. 1994. Annu. Rev. Biochem. 63:101–132.
Taylor, W. R. 1986. J. Theor. Biol. 119:205–218.
Telford, E. A., et al. 1995. J. Mol. Biol. 249:520–528.
Tiong, S. Y., and D. Nash. 1993. Genome. 36:924–34.
Tsujimoto, Y., et al. 1984. Science. 226:1097–1099.
Whitby, D., et al. 1995. Lancet. 346:799–802.
Wilson, R., et al. 1994. Nature. 368:32–38.
Wolf, J., et al. 1995. Int. J. Cancer. 60:5227–53.
Zhang, Y. J., et al. 1993. Biochem Biophys Res Commun. 196:1010–1016.
Zhong, W., et al. 1996. Proc. Natl. Acad. Sci. USA 93:6641–6646.

What is claimed is:

1. An isolated nucleic acid molecule comprising:

a nucleic acid sequence according to SEQ ID NO: 16; or a nucleic acid sequence which encodes the amino acid sequence according to SEQ ID NO:17.

2. The isolated nucleic acid molecule according to claim 1, wherein the nucleic acid molecule encodes a protein having kinase activity.

3. An isolated nucleic acid molecule comprising:

a nucleic acid sequence according to SEQ ID NO: 18; or a nucleic acid sequence which encodes the amino acid sequence according to SEQ ID NO:19.

4. An isolated nucleic acid molecule comprising:

a nucleic acid sequence according to SEQ ID NO:14; or a nucleic acid sequence which encodes the amino acid sequence according to SEQ ID NO:15.

* * * * *